US008961902B2

(12) United States Patent
Falb et al.

(10) Patent No.: US 8,961,902 B2
(45) Date of Patent: Feb. 24, 2015

(54) METHOD AND APPARATUS FOR ANALYTE PROCESSING

(75) Inventors: Peter W. Falb, Hingham, MA (US); David Brancazio, Cambridge, MA (US); Eric France, Quincy, MA (US); Brett P. Masters, Belmont, CA (US); Michael F. Miller, Hollis, NH (US); Joshua R. Ormsby, Boston, MA (US); Walker Sloan, Berlin, MA (US)

(73) Assignee: BioScale, Inc., Billerica, MA (US)

( * ) Notice: Subject to any disclaimer, the term of this patent is extended or adjusted under 35 U.S.C. 154(b) by 965 days.

(21) Appl. No.: 12/175,037

(22) Filed: Jul. 17, 2008

(65) Prior Publication Data

US 2009/0269248 A1 Oct. 29, 2009

Related U.S. Application Data

(60) Provisional application No. 61/047,377, filed on Apr. 23, 2008.

(51) Int. Cl.
*B01L 3/00* (2006.01)
*G01N 35/00* (2006.01)

(52) U.S. Cl.
CPC .......... *G01N 35/00029* (2013.01); *Y10T 29/49* (2015.01); *B01L 3/5025* (2013.01);
(Continued)

(58) Field of Classification Search
USPC ................................................. 422/102, 103
See application file for complete search history.

(56) References Cited

U.S. PATENT DOCUMENTS

| 4,848,722 A | 7/1989 | Webster ........................ 251/61.1 |
| 4,858,883 A | 8/1989 | Webster ........................ 251/61.1 |

(Continued)

FOREIGN PATENT DOCUMENTS

| WO | WO 99/33559 | 7/1999 |
| WO | WO 00/72970 | 12/2000 |

(Continued)

OTHER PUBLICATIONS

Galambos, Paul et al., "Precision Alignment Packaging for Microsystems with Multiple Fluid Connections," *Proceedings of 2001 ASME: International Mechanical Engineering Conference and Exposition*, Nov. 11-16, 2001.

(Continued)

*Primary Examiner* — Natalia Levkovich
(74) *Attorney, Agent, or Firm* — Proskauer Rose LLP

(57) ABSTRACT

A system for processing analytes in samples includes an instrument and a cartridge. The cartridge includes fluid inputs, input and output valve assemblies, processing devices, fluid reservoirs, and channels for carrying samples from the fluid inputs to the fluid reservoirs. The valve assemblies include valves adapted to form a sealed fluid chamber in response to force applied by a movable head assembly of the instrument. Each fluid reservoir is adapted to mate and align with an air displacement pump interface member. A valve assembly includes a recess wall surrounding a recess and a valve assembly wall surrounding both the recess and the recess wall. The recess wall and the valve assembly walls are adapted to mate with and seal against a flexible sheet covering the recess, the recess wall, and the valve assembly wall. The cartridge and instrument include complementary features for finely and coarsely aligning instrument assemblies with portions of the cartridge.

20 Claims, 22 Drawing Sheets

(52) U.S. Cl.
CPC ..... *B01L3/502715* (2013.01); *B01L 3/502738*
(2013.01); *B01L 2200/025* (2013.01); *B01L*
*2200/16* (2013.01); *B01L 2300/0816* (2013.01);
*B01L 2300/0654* (2013.01); *B01L 2400/0487*
(2013.01); *B01L 2400/0655* (2013.01); *G01N*
*2035/00148* (2013.01)
USPC ............ 422/503; 422/501; 422/502; 422/504

(56) References Cited

U.S. PATENT DOCUMENTS

| | | | | |
|---|---|---|---|---|
| 5,313,264 | A | 5/1994 | Ivarsson et al. | 356/73 |
| 5,496,009 | A | 3/1996 | Farrell et al. | 251/61.1 |
| 5,660,370 | A | 8/1997 | Webster | 251/129.17 |
| 5,851,004 | A | 12/1998 | Wu et al. | 251/331 |
| 5,863,502 | A | 1/1999 | Southgate et al. | 422/58 |
| 5,932,799 | A | 8/1999 | Moles | 73/53.01 |
| 5,962,081 | A | 10/1999 | Öhman et al. | 427/534 |
| 6,073,482 | A | 6/2000 | Moles | 73/53.01 |
| 6,293,012 | B1 | 9/2001 | Moles | 29/890.124 |
| 6,391,541 | B1 | 5/2002 | Petersen et al. | 435/5 |
| 6,440,725 | B1 | 8/2002 | Pourahmadi et al. | 435/288.5 |
| 6,581,899 | B2 | 6/2003 | Williams | 251/7 |
| 6,664,104 | B2 | 12/2003 | Pourahmadi et al. | 435/288.6 |
| 6,698,454 | B2 | 3/2004 | Sjölander et al. | 137/885 |
| 6,720,710 | B1 | 4/2004 | Wenzel et al. | 310/328 |
| 6,783,736 | B1 | 8/2004 | Taylor et al. | 422/103 |
| 6,793,753 | B2 | 9/2004 | Unger et al. | 156/155 |
| 6,818,185 | B1 | 11/2004 | Petersen et al. | 422/102 |
| 6,852,287 | B2 | 2/2005 | Ganesan | 422/99 |
| 6,877,528 | B2 | 4/2005 | Gilbert et al. | 137/827 |
| 6,878,540 | B2 | 4/2005 | Pourahmadi et al. | 435/287.2 |
| 6,881,541 | B2 | 4/2005 | Petersen et al. | 435/6 |
| 6,887,693 | B2 | 5/2005 | McMillan et al. | 435/173.7 |
| 6,893,879 | B2 | 5/2005 | Petersen et al. | 436/178 |
| 6,987,018 | B2 | 1/2006 | Taylor et al. | 435/286.7 |
| 7,168,675 | B2 | 1/2007 | Cabuz et al. | 251/7 |
| 7,169,314 | B2 | 1/2007 | Unger et al. | 216/22 |
| 7,223,371 | B2 | 5/2007 | Hayenga et al. | 422/100 |
| 2002/0019060 | A1 | 2/2002 | Petersen et al. | 436/514 |
| 2002/0128593 | A1 | 9/2002 | Sjolander et al. | 604/22 |
| 2002/0148992 | A1 | 10/2002 | Hayenga et al. | 251/61.1 |
| 2002/0166585 | A1 | 11/2002 | O'Connor et al. | 137/87.01 |
| 2003/0008308 | A1 | 1/2003 | Enzelberger et al. | |
| 2003/0196695 | A1 | 10/2003 | O'Connor et al. | 137/87.01 |
| 2004/0166031 | A1 | 8/2004 | Taylor et al. | 422/103 |
| 2004/0200909 | A1 | 10/2004 | McMillan et al. | 241/1 |
| 2004/0209354 | A1 | 10/2004 | Mathies et al. | 435/287.2 |
| 2005/0042137 | A1 | 2/2005 | Petersen et al. | 422/58 |
| 2005/0194316 | A1 | 9/2005 | Pourahmadi et al. | 210/638 |
| 2005/0201901 | A1 | 9/2005 | Grossman et al. | 422/100 |
| 2005/0221373 | A1* | 10/2005 | Enzelberger et al. | 435/6 |
| 2006/0027686 | A1 | 2/2006 | Taylor et al. | 241/2 |
| 2006/0030038 | A1 | 2/2006 | Taylor et al. | 435/306.1 |
| 2006/0076068 | A1 | 4/2006 | Young et al. | 137/829 |
| 2006/0257945 | A1 | 11/2006 | Masters et al. | 435/7.5 |
| 2006/0286685 | A1 | 12/2006 | Miller et al. | 436/526 |
| 2007/0037142 | A1 | 2/2007 | Sauer-Budge et al. | 435/5 |
| 2007/0037231 | A1 | 2/2007 | Sauer-Budge et al. | 435/7.32 |
| 2007/0042441 | A1 | 2/2007 | Masters et al. | 435/7.5 |
| 2007/0166199 | A1 | 7/2007 | Zhou et al. | 422/100 |
| 2007/0166200 | A1 | 7/2007 | Zhou et al. | 422/100 |
| 2007/0224084 | A1 | 9/2007 | Holmes et al. | 422/68.1 |

FOREIGN PATENT DOCUMENTS

| | | | |
|---|---|---|---|
| WO | WO 00/73412 | 12/2000 | |
| WO | WO 00/73413 | 12/2000 | |
| WO | WO 2005/111426 | 11/2005 | |
| WO | 2006/121997 | 11/2006 | ............ C12Q 1/68 |
| WO | WO 2006/119308 | 11/2006 | |
| WO | 2007/033385 | 3/2007 | |
| WO | WO 2007/030155 | 3/2007 | |
| WO | WO 2007/084425 | 7/2007 | |
| WO | 2008/055915 | 5/2008 | |

OTHER PUBLICATIONS

Linder, Vincent et al., "Reagent-Loaded Cartridges for aleless and Automated Fluid Delivery in Microfluidic Devices," *Analytical Chemistry*, vol. 77, No. 1, (Jan. 1, 2005) pp. 64-71.

* cited by examiner

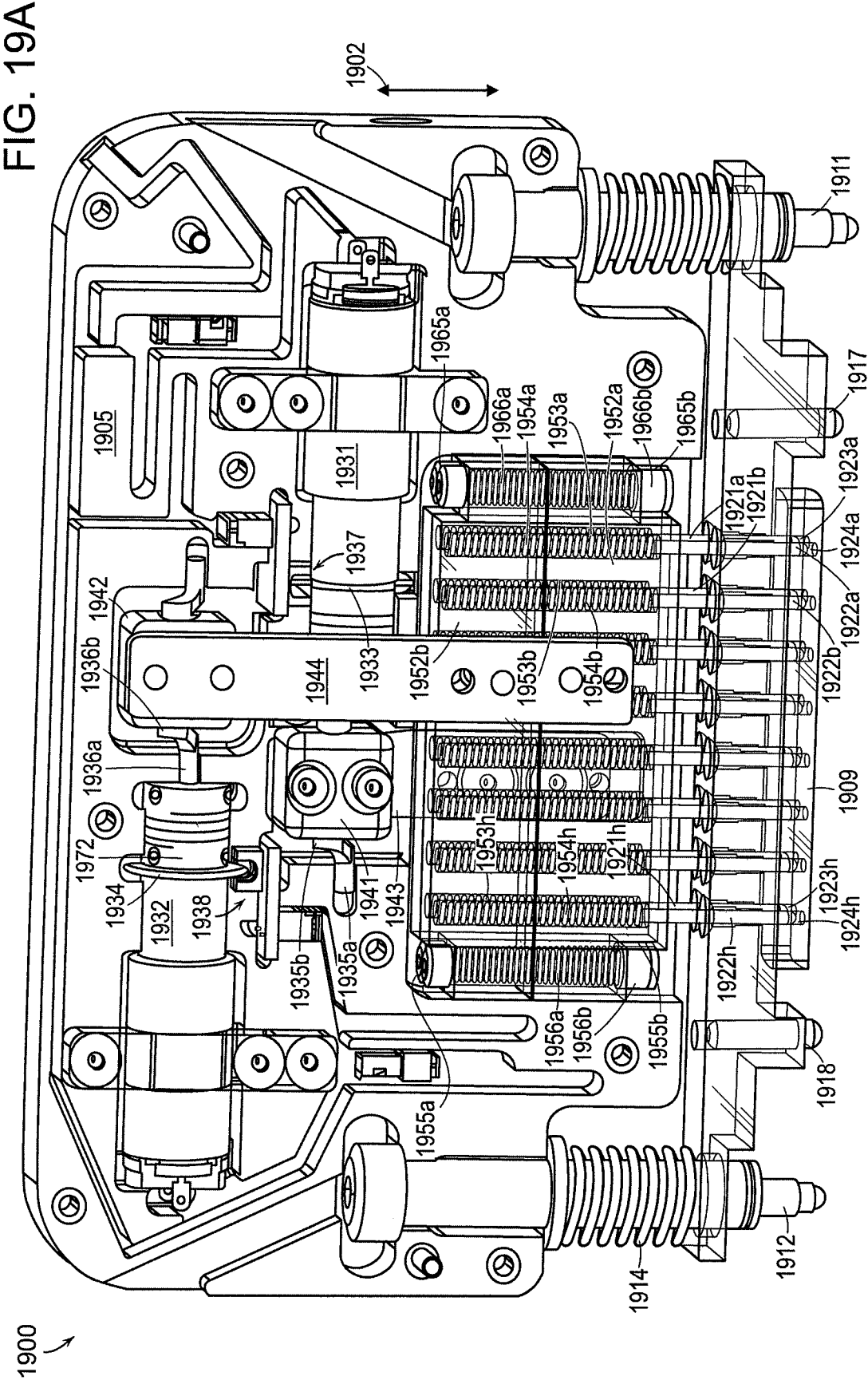

… (1 / 14)

METHOD AND APPARATUS FOR ANALYTE PROCESSING

CROSS-REFERENCE TO RELATED APPLICATIONS

This application claims priority to and the benefit of U.S. Provisional Patent Application Ser. No. 61/047,377, filed on Apr. 23, 2008, the entire contents of which are incorporated herein by reference.

TECHNICAL FIELD

The present invention relates to apparatus and methods for controlling the flow of fluid samples in a processing system, and in particular, apparatus and methods for detecting one or more analytes in fluid samples.

BACKGROUND OF THE INVENTION

Many systems have been developed to automate processes for detecting and/or analyzing analytes in a biological or chemical sample. Many of these systems, however, are inaccurate, prone to analyte sample contamination, and difficult to maintain and use. Many systems include structures for transporting samples to and from processing devices. These systems can quickly become contaminated. As a result, an entire system must be sterilized by, for example, autoclaving after each cycle. Some systems avoid this problem by using disposable cartridges. However, these cartridges are difficult and costly to manufacture. Also, many current systems use peristaltic pumping which, while functional, has several disadvantages. Due to manufacturing tolerances of peristaltic tubing, the peristaltic tubing needs to be batch calibrated in order to achieve the desired volume flow accuracy through the device. In addition, some systems configured for peristaltic tubing require the user to manipulate the tubing, which is a tedious task.

SUMMARY OF THE INVENTION

Systems according to the invention provide accurate analysis of fluid samples (biological, chemical or physical) and are easy to use and maintain. Some embodiments of the invention integrate a variety of fluid processing functions into a cartridge and replace peristaltic pumping with an air displacement system. Some embodiments include an instrument which interfaces with the cartridge to manage the transport and processing of fluid samples without directly contacting the fluid. Some embodiments of the cartridge incorporate features that enable valve operations and interfaces through which an instrument can form and actuate valves while pumping fluid samples through the cartridge. Some embodiments of the air displacement system interface with a cartridge to pull or push fluid samples through the cartridge. The cartridge, which is a consumable without peristaltic tubing, does not have to be calibrated regularly for accurate function.

The invention, in one aspect, relates to a cartridge for processing a sample. The cartridge includes a plurality of fluid inputs. The cartridge also includes an input valve assembly having a plurality of input valves. Each input valve has an inlet and an outlet and is adapted to form a sealed fluid chamber in response to force applied by a first movable head assembly. The cartridge also includes an output valve assembly that includes a plurality of first output valves and a plurality of second output valves. Each output valve has an inlet and an outlet and is adapted to form a sealed fluid chamber in response to force applied by a second movable (e.g., independently aligned) head assembly. The cartridge also includes a plurality of fluid reservoirs adapted to mate and align with a plurality of pump interface members. The cartridge also includes a plurality of processing devices, each of which has a fluid chamber, an inlet, and an outlet. Each processing device inlet is in fluid communication with the outlet of at least one input valve and each processing device outlet is in fluid communication with the inlet of a first output valve. Each first output valve outlet is in fluid communication with a fluid reservoir and the inlet of a second output valve. The cartridge also includes a plurality of channels. Each channel is adapted to transport a fluid sample from one fluid input, through one input valve of the input valve assembly, through one processing device, through one first output valve of the output valve assembly to one fluid reservoir and through one second output valve of the output valve assembly.

In some embodiments, the cartridge includes fluid reservoirs that are adapted to mate and align with one or more interface members of an air displacement pump. The air displacement pump can pull or push fluid samples into, through, and out of the cartridge. In one embodiment, the channels are adapted to transport a fluid sample (1) through an input valve of the input valve assembly, (2) through a processing device, (3) through a first output valve of the output valve assembly before emptying into the fluid reservoir. In some embodiments, additional channels are adapted to transport a processed sample from the fluid reservoir, through a second output valve of the output valve assembly, and out of the cartridge.

In another embodiment of the cartridge, each input and output valve is adapted to form a sealed fluid chamber in response to force applied by a mating surface of one of the first and second movable head assemblies. In one embodiment, each input and output valve is adapted to open and close fluid communication between the inlet and outlet in response to force applied by a corresponding movable member of one of first and second movable head assemblies.

In one embodiment, the processing devices are flexural plate wave devices. In another embodiment, the input valves include a plurality of reagent input valves and a plurality of fluid input (e.g., sample input) valves.

In another aspect of the invention, the cartridge includes at least one positioning feature. In one embodiment, the positioning feature positions the cartridge relative to an instrument for proper function of the analyte processing system. At least one positioning feature can include at least one aperture defined by a surface of the cartridge. A wall extending from the surface of the cartridge can surround the at least one aperture. In another embodiment, the at least one positioning feature includes at least one pin disposed on the surface of the cartridge. The at least one pin can mate with a corresponding aperture on an instrument. In some embodiments, the at least one positioning feature is adapted to align the cartridge with the instrument. In another embodiment, at least a second positioning feature is adapted to align at least one assembly of the instrument with at least one portion of the cartridge. In one embodiment, the at least one assembly is the first movable head assembly and the at least one portion of the cartridge is the input valve assembly.

In one embodiment of the invention, each fluid reservoir includes a chamber having an aperture and a wall. The wall extends from an exterior surface of the chamber and surrounds the aperture. The wall is adapted to align, mate, and seal with one of the plurality of pump interface members. In another embodiment, the wall is adapted to receive a gas permeable, liquid impermeable element. In yet another embodiment, the wall is adapted to receive a filter or membrane element to prevent liquid or liquid vapor from entering an air pump system which interfaces with the fluid reservoir.

The invention, in another aspect, is a cartridge for processing a sample. The cartridge includes a body having a first side and a second side opposite the first side. The first side of the body includes first and second channels. The second side of the body includes a first recess having first and second apertures. The first recess is in fluid communication with (1) the first channel via the first aperture and (2) the second channel via the second aperture. The cartridge further includes a first recess wall that surrounds the first recess and is adapted to mate with and seal against a flexible sheet covering the first wall and the first recess when the cartridge is installed in a sample processing system. In one embodiment, the first channel is in fluid communication with a first fluid input and the second channel is in fluid communication with a processing device.

In another embodiment, the cartridge further includes a valve assembly wall which surrounds the combination of the first recess and the first recess wall. The valve assembly wall is adapted to mate with and seal against the flexible sheet.

In another embodiment, the first side of the cartridge body further includes a third channel and the second side of the cartridge includes a second recess. In this embodiment, the second recess is in fluid communication with (1) the third channel via the first aperture of the second recess and (2) the first channel via the second aperture of the second recess. A second recess wall surrounds the second recess. Also, the valve assembly wall surrounds the combination of the second recess and the second recess wall. A surface of the second recess wall is adapted to mate with and seal against a flexible sheet covering the second recess wall and the second recess when installed in a sample processing system.

In another embodiment of the cartridge, the first channel is in fluid communication with a fluid reservoir, the second channel is in fluid communication with a processing device, and the third channel is in fluid communication with a waste output interface.

In one embodiment, the cartridge includes a sheet which is adhered to the first side of the body at least partially enclosing at least one feature of the cartridge. In some embodiments, the at least one feature includes the first channel and the fluid reservoir.

The invention, in another aspect, relates to a system for processing a sample. The system includes a cartridge with a plurality of fluid interfaces, a valve assembly, a plurality of channels, and a plurality of fluid reservoirs. The valve assembly includes a plurality of valves, each of which has an inlet and an outlet. At least one channel provides fluid communication between at least one fluid interface and at least one fluid reservoir through at least one valve. The system also includes a movable head assembly. The movable head assembly includes a valve interface assembly adapted to apply a force to the valve assembly to form a sealed fluid chamber in each of the plurality of valves. The valve interface assembly includes a plurality of movable members that are adapted to open and close fluid communication between the inlet and outlet of each of the plurality of valves. The system also includes a pump. The pump includes a plurality of pump interface members each adapted (1) to mate and align with a corresponding one of the plurality of fluid reservoirs and (2) to move a sample between at least one fluid interface and at least one fluid reservoir through at least one channel and at least one valve. In one embodiment, a movable member applies a force to a valve to close fluid communication between the inlet and outlet of the valve. In another embodiment, each movable member is adapted to provide zero-hold power actuation to each corresponding valve.

The invention, in another aspect, relates to an instrument for processing a sample. The instrument includes a plate, a moveable head assembly, and a pump. The plate is adapted to receive and to support a cartridge. The movable head assembly includes a valve interface assembly adapted to apply a force to a valve assembly on the cartridge to form a sealed fluid chamber in at least one valve in the valve assembly. The valve interface assembly includes at least one movable member adapted to open and close fluid communication between an inlet and outlet of the at least one valve. The pump includes a plurality of pump interface members adapted to mate and align with a plurality of fluid reservoirs defined on the cartridge.

In one embodiment of the instrument, the movable head assembly includes at least one positioning feature adapted to mate and align with at least one complementary positioning feature defined on the cartridge. In another embodiment of the instrument, the valve interface assembly includes at least one positioning feature adapted to mate and align with at least one complementary positioning feature associated with the valve assembly of the cartridge. In some embodiments, the plate is a movable plate. In some embodiments, the plate is a thermally controlled plate.

The invention, in another aspect, relates to a method of processing a sample with a cartridge. The method includes applying a force to a flexible sheet disposed over a plurality of input valves and a plurality of output valves to provide a sealed chamber in each of the input and output valves. The plurality of input valves include a plurality of reagent input valves and a plurality of fluid input valves. The plurality of output valves include a plurality of first and second output valves. The plurality of reagent input valves and the plurality of second output valves are closed. Also, the plurality of fluid input valves and the plurality of first output valves are opened. A sample is drawn through each fluid input valve, through a corresponding processing device and through a corresponding first output valve. The samples are processed by each processing device. After the samples are processed, the plurality of fluid input valves are closed and the plurality of reagent input valves are opened. A reagent is drawn through (1) each reagent input valve, (2) a corresponding processing device, and (3) a corresponding first output valve. The flow of the reagent causes each of the samples to enter a corresponding fluid reservoir. The plurality of first output valves are closed and the plurality of second output valves are opened. The sample and the reagent are pushed out of each fluid reservoir and through each second output valve.

In some embodiments, drawing a sample and a reagent through the cartridge is repeated many times before pushing the sample and the reagent out of each fluid reservoir and through each second output valve.

The invention, in another aspect, relates to a method of manufacturing a cartridge for processing a sample. The method includes forming a first channel and a second channel in a first side of a body. A first recess is formed in a second side of the body. A first aperture is formed in the first recess in fluid communication with the first channel. A second aperture is formed in the first recess in fluid communication with the second channel. A first recess wall is formed surrounding the first recess. The first recess wall mates with and seals against a flexible sheet covering the first recess wall and the first recess when the cartridge is installed in a sample processing system.

In one embodiment, the method of manufacturing a cartridge includes forming a valve assembly wall (1) surrounding the combination of the first recess and the first recess wall and (2) mating with and sealing against the flexible sheet. In some embodiments, the flexible sheet permanently seals against the valve assembly wall without the use of an adhesive. In some embodiments, one or more manufacturing steps are performed together.

In another embodiment, the method of manufacturing a cartridge further includes forming a third channel in the first side of the body. A second recess is formed in the second side of the body. A first aperture is formed in the second recess in fluid communication with the third channel. A second aperture is formed in the second recess in fluid communication with the second channel. A second recess wall is formed surrounding the second recess and mating with and sealing against the flexible sheet, which covers the second recess wall and the second recess, when the cartridge is installed in a sample processing system. In one embodiment, a valve assembly wall is formed surrounding the combination of the first and second recesses and the first and second recess walls and mating with and sealing against the flexible sheet.

The details of one or more examples are set forth in the accompanying drawings and the description below. Further features, aspects, and advantages of the invention will become apparent from the description, the drawings, and the claims.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

FIG. 19A is a perspective side view of a valve actuator assembly with the front cover removed, according to another illustrative embodiment of the invention.

DETAILED DESCRIPTION OF THE INVENTION

Figure 1:
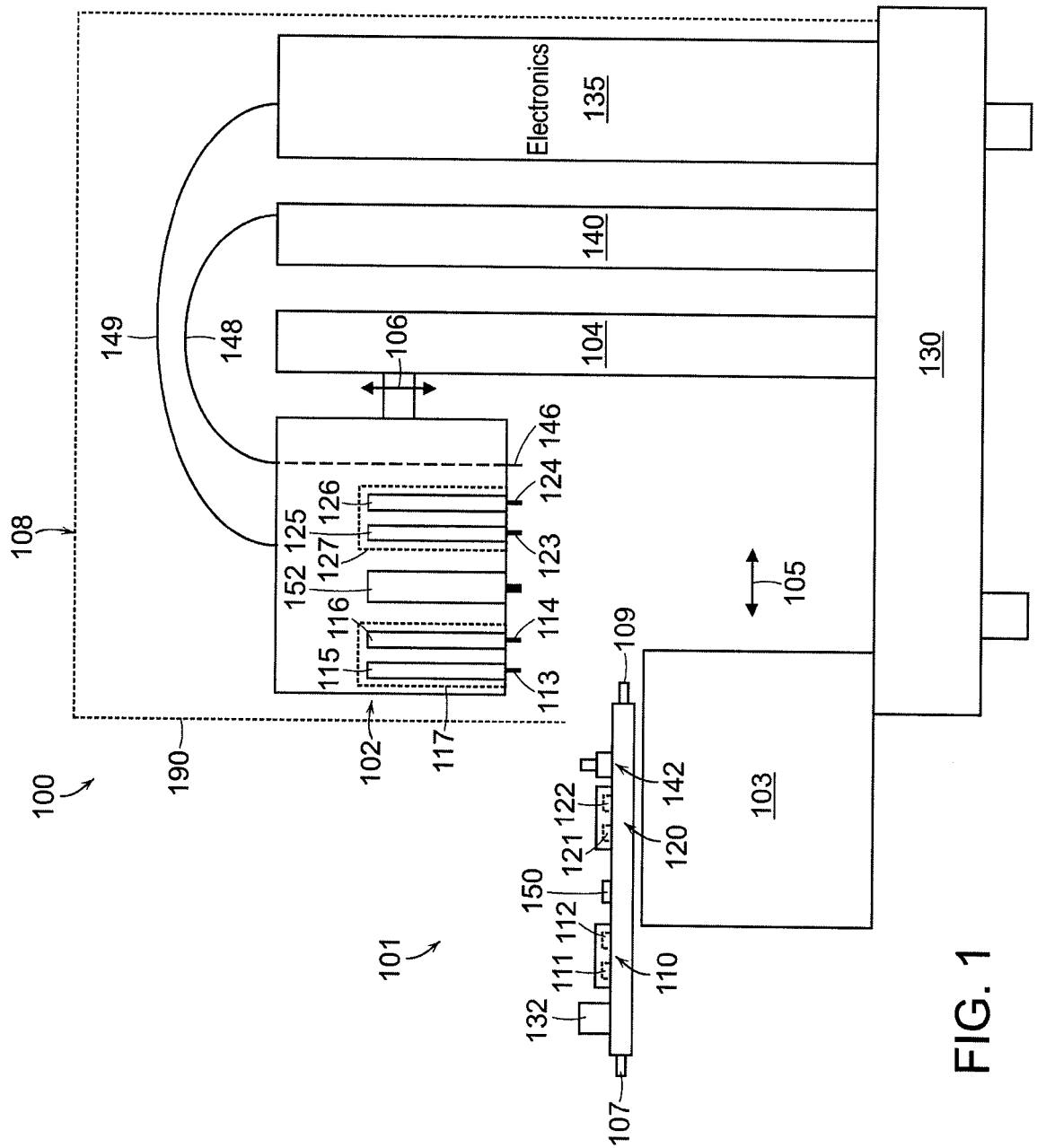
FIG. 1 is a block diagram of a system for processing a sample, according to an illustrative embodiment of the invention.

Generally, the invention relates to a replaceable fluidic cartridge for analyzing one or more samples and an instrument for operating the cartridge. FIG. 1 is a block diagram of a system 100 for processing a sample, according to an embodiment of the invention. The system 100 includes a cartridge 101 and an instrument 108. The instrument 108 includes a base 130 which supports electronics 135 and an air control device 140. The instrument 108 also includes a head assembly 102 movable along a vertical axis 106 and an elevator assembly 104 that supports and drives the motion of the movable head assembly 102. The instrument 108 also includes a platform 103 movable along the horizontal axis 105. The movable head assembly 102 includes a first movable head assembly 117 and a second movable head assembly 127. To operate the system 100, a user places the cartridge 101 on the platform 103 and moves the platform 103 with the cartridge 101 to a location under the head assembly 102. The user then sends a command signal to the electronics 135 (e.g., via a computer or other user interface in communication with the electronics 135) to move the head assembly 102 into engagement with the cartridge 101. After the head assembly 102 engages with the cartridge 101, the user deposits a sample into the cartridge 101 and sends a command signal to the electronics 135 to execute a series of processing steps. The head assembly 102 then operates the cartridge 101 to process the samples through the cartridge 101 in accordance with the series of processing steps.

The cartridge 101 includes a fluid input 132, a buffer input 107, an input valve assembly 110, a processing device 150, an output valve assembly 120, a fluid reservoir 142, and a waste output 109. The input valve assembly 110 includes a fluid input valve 112, which controls the flow of a sample from the fluid input 132 to the processing device 150. The input valve assembly 110 also includes a reagent input valve 111, which controls the flow of reagent between the reagent input 107 and the processing device 150. Each input valve is constructed so that it forms a sealed fluid chamber when the first movable head assembly 117 applies a force to each input valve. In one embodiment, the processing device 150 detects analytes in a sample.

The output valve assembly 120 features a first output valve 121, which controls the flow of the sample exiting the processing device 150 which is directed to the fluid reservoir 142. The output valve assembly 120 also includes a second output valve 122, which controls the flow of the sample between the fluid reservoir 142 and the waste output 109. Each output valve is constructed so that it forms a sealed fluid chamber when the second movable head assembly 127 applies a force to each input valve.

The head assembly 102 includes a plurality of valve actuator assemblies 115, 116, 125, 126 that open and close the valves 111, 112, 121, 122 of the cartridge 101 to control the transport of a sample or reagent through the cartridge 101. A reagent input valve actuator assembly 115 moves a pin 113 along the direction of the vertical axis 106 to open and close the reagent input valve 111. A fluid input valve actuator assembly 116 moves a pin 114 along the direction of the vertical axis 106 to open and close the fluid input valve 112. A first output valve actuator assembly 125 moves a pin 123 along the direction of the vertical axis 106 to open and close the first output valve 121. A second output valve actuator assembly 126 moves a pin 124 along the direction of the vertical axis 106 to open and close the second output valve 122.

The instrument 108 also includes the air pump 140 that interfaces with the fluid reservoir 142 and uses air to push or pull fluids through the cartridge 101. Tubing 148 connects the air pump 140 to a pump interface member 146. The pump interface member 146 couples to the fluid reservoir 142. The instrument 108 also includes a processing device interface 152. The processing device interface 152 is electrically coupled to the processing device 150. The electronics 135 are electrically coupled to the processing device interface 152 through an electrical cable 149 between the electronics 135 and the movable head assembly 102. The electronics 135 operate the processing device 150 and obtains measurement data from the processing device 150 through the processing device interface 152. The electronics 135 also provide electrical power and control signals to the elevator assembly 104, the air pump 140, the cartridge platform 103 and the valve actuator assemblies 117, 118 and processing device interface 152 of the movable head assembly 102. The instrument 108 includes a cover 190 that encloses and protects the movable head assembly 102, the elevator assembly 104, the air pump 140, and the electronics 135 and provides a clean environment in which to operate the cartridge 100.

The elevator assembly 104 includes an elevator mechanism that raises and lowers the head assembly 102. In some embodiments, the elevator assembly 104 also includes position sensors used to enable, stall and terminate motion of the head assembly 102. In some embodiments, the instrument 108 includes access door sensors that provide information as to whether or not access doors (not shown, but, for example a portion of cover 190) to the instrument 108 are open. In one embodiment, the information is an interrupt signal. A user may program the electronics 104 with logic that combines information from the position sensors with information from the access door sensors to stop the motion of, or limit the force applied by, the head assembly 102 to decrease the risk of injury to the user (e.g., the head assembly 102 crushing the user's hand or fingers). In one embodiment, the instrument 108 includes force sensors. The force sensors provide force information used to control the force applied by the head assembly 102. In another embodiment, the instrument 108 includes current sensors that sense the current applied to the motors of the instrument 108 that move the head assembly 102. Current information from the current sensor is used to control or limit the force applied by the motors that move the head assembly 102.

Figure 2:
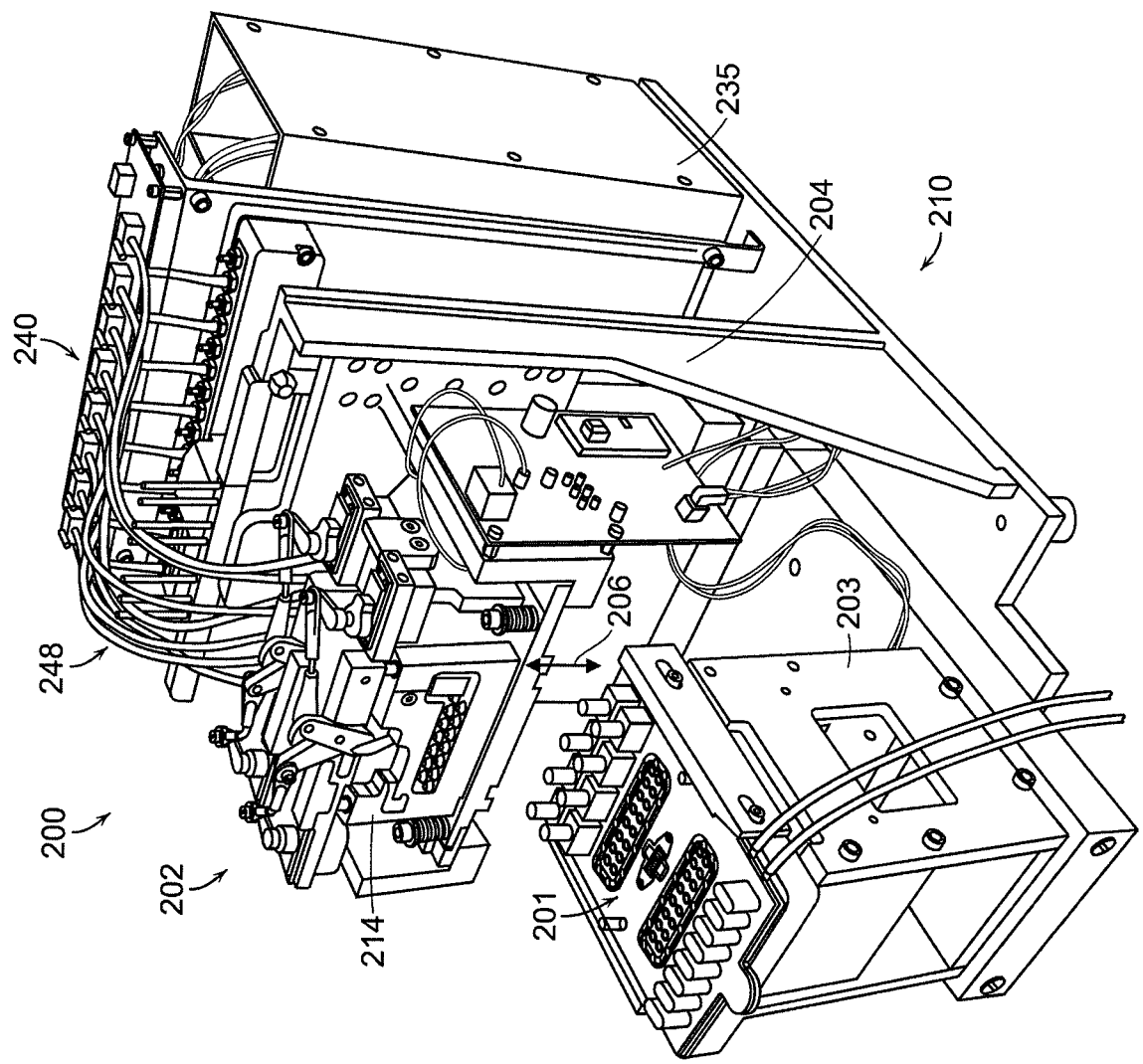
FIG. 2 is a perspective view of a system for processing an sample, according to an illustrative embodiment of the invention.

FIG. 2 is a perspective view of a system 200 for processing an analyte sample, according to an another embodiment of the invention. System 200 is configured to process multiple samples in parallel. The system 200 is also configured to process eight samples simultaneously. The system 200 includes a cartridge 201 with eight processing channels and an instrument 210. The system 200 includes a movable head assembly 202 and an elevator assembly 204 for moving the movable head assembly 202 in a vertical direction 206. The system 200 also includes a syringe pump assembly 240 with eight syringe pumps. Each of the syringe pumps provides air control to one of a plurality of pump interface members (not shown) on the movable head assembly 202 via one of a plurality of tubes 248. The movable head assembly 214 includes a valve actuator assembly 214, which mates with a corresponding valve assembly on the cartridge 201. The system 200 includes system electronics 235 that provide power and control signals to electronic devices in the system.

Figure 3A:
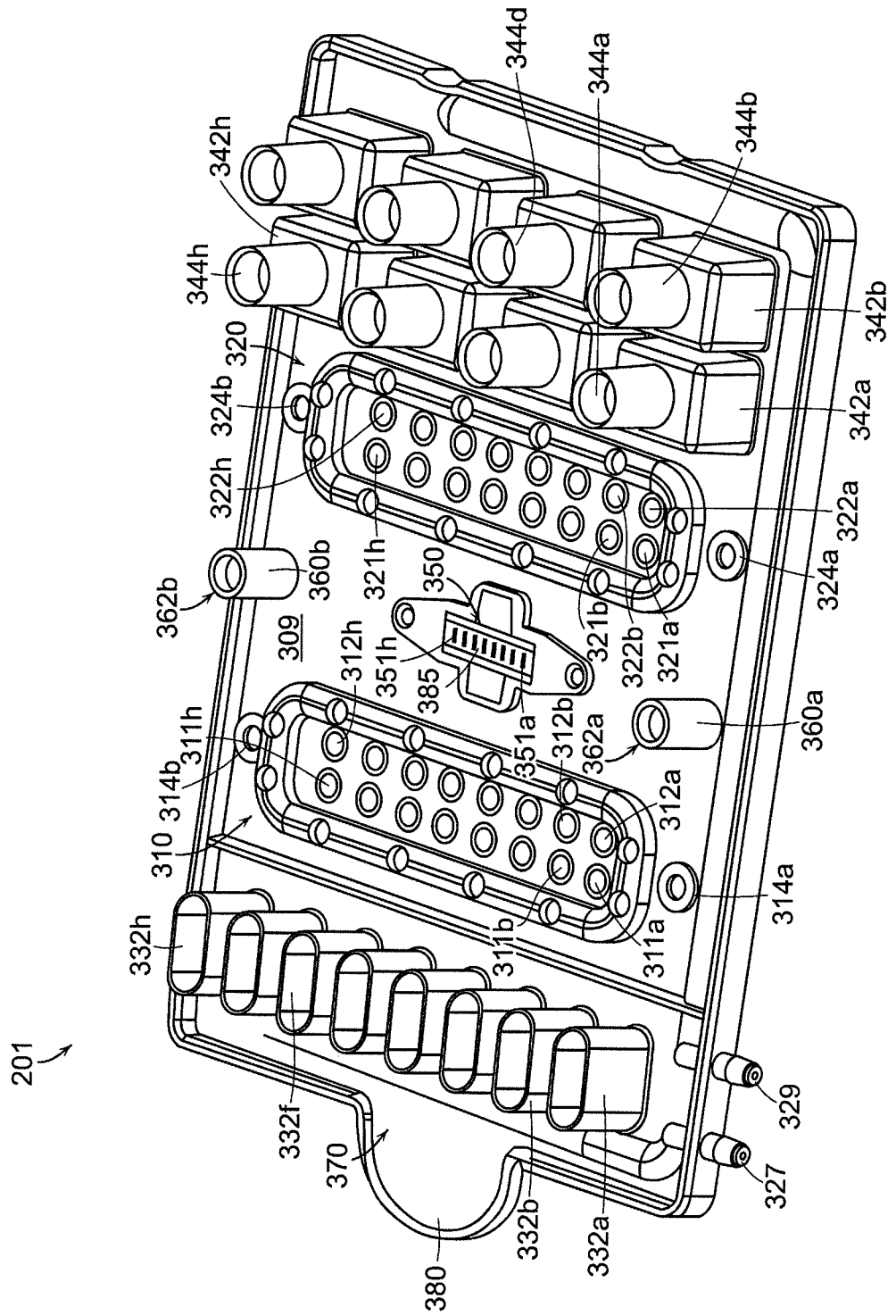
FIG. 3A is a perspective view of the cartridge in FIG. 2 having a plurality of fluid inputs, a plurality of input and output valves, a plurality of processing devices, and a plurality of reservoirs, according to an illustrative embodiment of the invention.
Figure 3B:
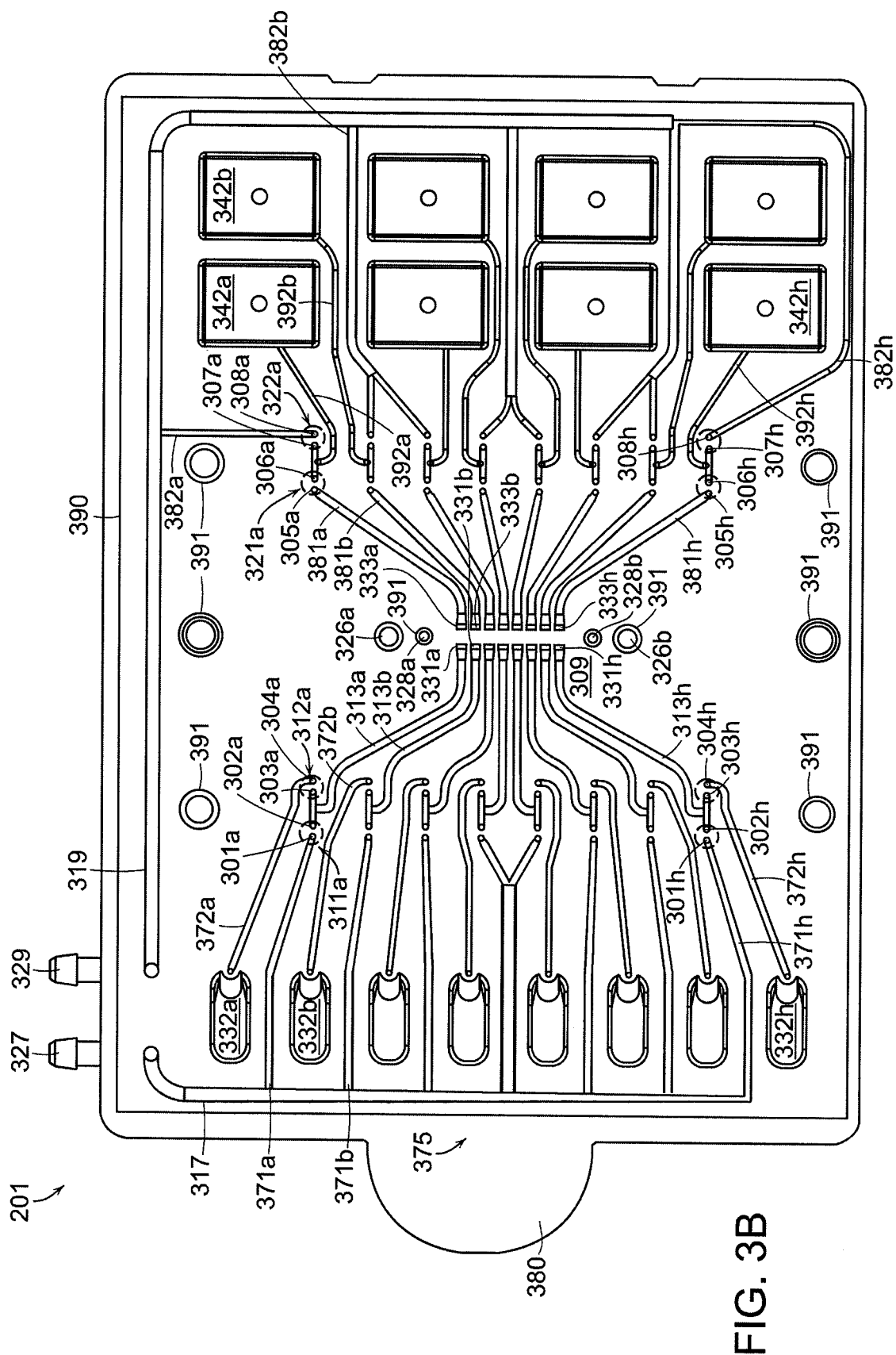
FIG. 3B is a bottom view of the cartridge of FIG. 3A.

FIGS. 3A and 3B illustrate the details of the cartridge 201 in the analyte processing system 200 of FIG. 2. The cartridge 201 includes a plurality of fluid inputs 332a-332h (generally, 332) and an input valve assembly 310 having a plurality of fluid input valves 312a-312h (generally, 312). The cartridge 201 also includes a chip 350 having a plurality of processing devices 351a-351h (generally, 351) and an input valve assembly 310 having a plurality of fluid input valves 312a-312h (generally, 312) having a plurality of first output valves 321a-321h (generally, 321). The cartridge 201 also includes a plurality of fluid reservoirs 342a-342h (generally, 342), and a plurality of channels 372a-372h, 313a-313h, 381a-381h, and 342a-342h for transporting fluid samples from the fluid inputs 332 to the fluid reservoirs 342. In some embodiments, the fluid reservoirs 342 serve as transfer chambers that both receive and expel fluid. In another embodiment in which the cartridge 201 is for single use only, the fluid reservoirs 342 only receive and store fluid.

Each fluid input valve 312 has inlets 303a-303h and outlets 304a-304h through which fluids flow from a fluid input channel 372 to a processing device input channel 313. Similarly, each reagent input valve 311 has inlets 301a-301h (generally, 301) and outlets 302a-302h through which fluids flow from a reagent input channel 371a-371h (generally, 371) to a processing device input channel 313. On the output side of the cartridge 201, each first output valve 321 has inlets 305a-305h and outlets 306a-306h through which fluids flow from a processing device output channel 381 to a fluid reservoir channel 392. Similarly, each second output valve 322 has inlets 307a-307h and outlets 308a-308h through which fluids flow from the fluid reservoir channel 392 to a waste output channel 382. The cartridge further includes a waste output interface 329, a plurality of second output valves 322a-322h (generally, 322), and a plurality of waste output channels 382a-382h (generally, 382) for transporting waste fluid from the fluid reservoirs 342 to the waste output interface 329.

In this embodiment, the waste output interface 329 includes a barb for coupling to a flexible piece of tubing. In one embodiment, a flexible piece of tubing is connected from the waste output interface 329 to a bottle or other container for collecting waste fluid from the fluid reservoirs 342. The cartridge 201 also includes a reagent input interface 327 through which a reagent may flow towards the fluid reservoirs 342 via reagent input channels 371a-371h (generally, 371). In one embodiment, a flexible piece of tubing connects the reagent input interface 327 to a bottle, degassed bag, or other container, which contains a buffer solution. The flexible piece of tubing may have a check valve to prevent back flow from the reagent input interface 327 to a bottle of buffer solution.

The processing chip 350 is disposed on the body 309 of the cartridge 201. In one embodiment, the processing chip 350 is attached to a surface of the body 309 of the cartridge 201 using an adhesive. The cartridge 201 includes a processing device inlet 331a-331h (generally, 331) and a processing device outlet 333a-333h (generally, 333), which interface with the channel of each processing device 351. The processing chip 350 is precisely disposed on the body 309 of the cartridge 201 so that each processing device 351 properly aligns with each processing device inlet 331a-331h and each processing device outlet 333 of the cartridge 201. In various embodiments, the chip 350 mounts on a raised surface or a recess defined by the cartridge 201 to ensure proper alignment with the processing device inlets 331a-331h and outlets 333.

In another embodiment, the processing chip 350 is mounted and sealed with a pressure sensitive adhesive that has apertures that align with the cavities of each processing device 351 and each processing device inlet 331 and outlet 333. In some embodiments, the surface of each processing device 351 is capped with a thin laminate (a cap 385) made from pressure sensitive adhesive and acrylic backing sheets. In one embodiment, the cap 385 forms a low profile pocket between the cap 385 and the surface of the processing device 351. The processing device cap 385 protects a sample processing system (e.g., the sample processing system 200 of FIG. 2) from liquid contamination if a membrane of the processing device 351 were to break. In some embodiments, the cap 385 is designed to allow the processing device interface (e.g., the processing device interface 152 in FIG. 1) to electrically access contact pads on the processing device 351. The cap 385 is further designed to allow a processing device interface and/or a movable head assembly (e.g., the movable head assembly 202 of FIG. 2) to position components (e.g., a magnet) of the processing device interface as close as possible to the surface of the processing device without mechanically interfering with the cap 385.

In one embodiment, the processing devices 351 are sensors for detecting an analyte in a sample or sensing a property of a sample. In another embodiment, the processing devices 351 are flexural plate wave (FPW) devices. In one embodiment, the chip 350 of processing devices 351 is a micro-electromechanical system (MEMS) chip.

Fluid is pushed or pulled through components of the cartridge 201 at prescribed rates using an air control device, which is in fluid communication with the fluid reservoirs 342 through pump interface members 344a-344h (generally, 344). In one embodiment, the air control device is an air displacement pump. In another embodiment, the air control device is a standard syringe pump. The standard syringe pump includes a barrel and a plunger that moves in two directions inside the barrel. A motor or other mechanism drives the plunger in two directions inside the barrel to either push or pull samples and reagents through the channels and devices (e.g., processing devices 351 and second output valves 322) of the cartridge 201. Each fluid reservoir 342 is in fluid communication with a separate air control device. In another embodiment, all fluid reservoirs 342 are in fluid communication with a single air control device. The fluid reservoirs 342 accumulate the samples and reagents that an air control device draws through the cartridge 201 and into the fluid reservoirs 342 by pulling air out of the fluid reservoirs 342. When the fluid reservoirs 342 fill to a predetermined level or fill to capacity, the air control device pushes air into the fluid reservoirs 342 to displace the samples and reagents out of the fluid reservoirs 342.

To perform an analysis of a sample using the cartridge 201, the sample is deposited into the fluid input 332. An air control device that interfaces with the fluid reservoirs 342 through pump interface members 344, draws the sample from the fluid input 332 through a fluid input channel 372. The air control device then draws the sample into the fluid input valve 312 via the inlet 303. The sample exits the fluid input valve 312 through the outlet 304 into a processing device input channel 313a-313h leading to the inlet 331a-331h of the processing device 350. The sample passes through a processing device 351, which analyzes the sample, and exits through an outlet 333 into a processing device output channel 381.

The processing device output channel 381 leads to the inlets 305a-305h (generally, 305) of the first output valve 321. The sample passes into the first output valve 321 via inlet 305 and exits via an outlet 306a-306h (generally, 306) into a fluid reservoir channel 392 and flows towards the fluid reservoir 342. The processed sample accumulates in the fluid reservoir 342 until the reservoir 342 is filled with a predetermined volume of the processed sample. The air control device then pushes the contents of the fluid reservoir 342 back into the fluid reservoir channel 392 towards an inlet 307a-307h (generally, 307) of the second output valve 322. The processed sample then flows into the second output valve 322 via the inlet 307 and exits into a waste output channel 382 via an outlet 308a-308h (generally, 308) of the second output valve 322. The samples in the waste output channels 382 flow into a common waste output channel 319 and exit the cartridge 201 through the waste output interface 329.

The air control device may also separately draw a reagent through a reagent interface 327 into a common reagent input channel 317. The reagent flows from the common reagent input channel 317 into a plurality of reagent input channels 371 towards inlets 301 of the reagent input valves 311. The reagent enters the reagent input valve 311 via the inlet 301 and exits the reagent input valve 311 through the outlet 302 into the processing device input channel 313 towards the processing device inlet 331a-331h of the processing device 350. The reagent may then follow the same path described above with respect to the sample. The reagent may include a buffer solution for cleansing the cartridge channels and components in preparation for the next sample processing run.

In other embodiments, the fluid reservoirs 342 or additional sets of fluid reservoirs and corresponding interfaces to an air control device are disposed at another location along the fluid path from the input to the output of the cartridge 201. For example, in one embodiment, an additional set of fluid reservoirs may be disposed between the input valve outlets 302, 304 and the processing device inlets 331 of the processing device 350 to receive and combine a given amount of reagent from the common reagent input channel 317 with a given amount of a sample from the fluid input 332. In this embodiment, an additional valve is disposed between each additional fluid reservoir and each processing device inlet 331 to prevent damage to each processing device 351 from the pressures applied by an air control device coupled to each additional fluid reservoir. In this embodiment, after the additional valve is closed, each air control device coupled to each additional fluid reservoir draws fluid separately or simultaneously from the fluid input 332 and the common reagent input channel 317 into each additional fluid reservoir. Then, the additional valve is opened and each air control device expels the mixture from each additional fluid reservoir toward the inlets 332 of the processing device 350.

Referring to FIG. 2 and FIG. 3A, the cartridge 201 can include both coarse and fine positioning features to properly position the movable head assembly 202 and its components with respect to the cartridge 201 and its components. The positioning features can include apertures defined by the body 309 of the cartridge 201 or pins disposed on the body 309 of the cartridge 201. In one embodiment, the positioning apertures mate with a complementary locating pin on the movable head assembly 202. As shown in FIG. 3A, the cartridge 201 includes two coarse positioning members 360a, 360b. In this embodiment, the coarse positioning members 360a, 360b include an aperture defined by the surface of the cartridge 201 and a wall surrounding the aperture and extending from the surface of the cartridge 201. The coarse positioning members 360a, 360b roughly align the movable head assembly 202 relative to the cartridge 201 in a plane parallel to the surface of the cartridge 201.

In another embodiment, when the movable head assembly 202 engages with the cartridge 201, a surface of the movable head assembly 202 rests on the top portion 362a, b of the walls of the coarse positioning members 360a, 360b. In this way, the walls of the coarse positioning members 360a, 360b align the movable head assembly with respect to the cartridge 201 along the vertical direction 206 perpendicular to the top surface 370 of the body 309 of the cartridge 201.

As shown in FIG. 3A, the cartridge 201 also includes input valve assembly positioning apertures 314a, 314b and output valve assembly positioning apertures 324a, 324b defined in the body 309 of the cartridge 201. The input valve assembly positioning apertures 314a, 314b finely position a movable head assembly's input valve assembly interface relative to the input valve assembly 310 of the cartridge 201. Likewise, the output valve assembly positioning apertures 324a, 324b finely position a movable head assembly's output valve assembly interface relative to the output valve assembly 310 of the cartridge 201. In some embodiments, the movable head assembly's valve assembly interfaces can align with the cartridge's valve assemblies 310, 320 to within a few thousandths of an inch.

Referring to FIG. 3B, the cartridge 201 also includes processing device positioning apertures, 326a, 326b, 328a, 328b defined by the surface of the body 309 of the cartridge 201. The processing device positioning apertures 326a, 326b, finely position the movable head assembly's processing device interface relative to the processing device 350 so the processing device 350 properly functions and transmits and receives measurement and control signals. In one embodiment, the processing device positioning apertures 328a, 328b position a fixture (with complementary pins) that is used to attach the processing device chip 350 to the body 309 of the cartridge 201 and to apply the cap 385 to the top surface of the processing device chip 350 during assembly.

In various embodiments, the body 309 of the cartridge 201 is fabricated by injection molding. In one embodiment, the body 309 is injection molded to form the fluid inputs 332, portions of the fluid reservoirs 342, portions of the input valves 311, 312 and the output valves 321, 322 (e.g., the valve recesses and recess walls described below), and the channels 313, 317, 319, 371, 372, 381, 382, 392. In one embodiment, the cartridge 201 is formed of injection molded polycarbonate with the channels formed on the bottom side 375 of the body 309 and the fluid inputs 332, portions of the fluid reservoirs 342, and portions of the input valves 311, 312 and the output valves 321, 322 formed on the top side 370 of the body 309. The body 309 can be formed from a variety of materials, including plastics, elastomers, metals, ceramics, or composites, among other materials. In some embodiments, polymers (e.g., polycarbonate) can be employed to make the body 309.

To assemble the cartridge 201, the body 309 is submerged in an ethanol solution containing from about 5% to about 100% ethanol for a time interval ranging from about 2 minutes to about 30 minutes. In one embodiment, each cartridge 201 channel is not a tunnel defined through the body 309, but rather is an extended cavity cut through a surface of the body 309. A surface of the body 309 through which the channels 313, 371, 372, 381, 382, 392 are disposed and/or cut, for example, the surface of the bottom side 375 of the body 309 is positioned to enable the ethanol solution to drain from the channels of cartridge 201. In some embodiments, the surface of the bottom side 375 of the body 309 is positioned on a surface, for example, on a non-abrasive tissue (e.g., a Kimwipe®). Optionally, any particles are removed from the surface of the bottom side 375 of the body 309 by cleaning the surface of the bottom side 375 by, for example, blowing an inert gas, such as nitrogen, over the surface of the bottom side 375. A sealing layer 390 is disposed on at least a portion of a surface of the body 309. For example, the sealing layer 390 is disposed on the bottom side 375 of the body 309 (see also FIG. 6).

In some embodiments, the sealing layer 390 is a thermal transfer layer. The sealing layer 390 can be a thin layer that measures between about 0.00254 mm (0.0001 in) and 0.254 mm (0.01 in), or between about 0.0254 mm (0.001 in) and 0.127 mm (0.005 in). The sealing layer 390 provides a thermal interface layer that allows for fluid thermal conditioning. For example, temperature of wash buffers, the fluid, the sample specimen and/or the sample can be controlled or regulated prior to processing by the processing device 351. More specifically, when the sealing layer 390 contacts a thermally controlled surface (e.g., a top surface of a plate 1604 that has a temperature control device 1606; see FIGS. 16A and 16B) the liquid flowing through the cartridge 201 is thermally conditioned. Thermal conditioning of liquids (e.g., wash buffers, the fluid, the sample specimen and/or the sample) impacts and/or controls the viscosity, density, and speed of sound of the liquid flowing through the cartridge 201.

In one embodiment, the sealing layer 390 has one or more portions 391 that align with the positioning features 314a, 314b, 324a, 324b, 325a, 325b, 326a, 326b, 360a, 360b defined by the body 309. For example, a portion of the sealing layer 390 includes apertures 391 that align with the positioning apertures 314, 324 defined by the body 309. Thus, the sealing layer can be properly positioned and attached to the surface of the bottom side 375 of the body 309 by aligning the apertures in the sealing layer 390 with corresponding apertures defined in the body 309. In one embodiment, the sealing layer 390 is a hydrophilic layer. Suitable materials that can be employed as a sealing layer 390 include a hydrophilic tape or a plastic film such as polyester, polycarbonate, polyimide, or polyetherimide with a hydrophilic seal. In one embodiment, the sealing layer 390 provides a wetted surface that is disposed on a surface of the body 309. The sealing layer 390 can be, for example, a hydrophilic tape. In another embodiment, a surface of the body 309 is modified, for example, chemically and/or by introducing a charge to the surface of the body 309. For example, the surface of the body 309 can be treated with a fluid to effect hydrophobic or hydrophilic characteristics on the surface of the body 309.

In one embodiment, the sealing layer 390 is a hydrophilic tape that includes an adhesive. A backing is removed from the hydrophilic tape and is discarded. A region of the hydrophilic tape is aligned with the positioning features defined by the body 309. The adhesive side of the hydrophilic tape is pressed onto the surface of the bottom side 375 of the body 309. In one embodiment, the sealing layer 390 is rubbed with a block, for example, a plastic block to ensure that there are no bubbles between the sealing layer 390 and the surface of the bottom side 375 of the body 309. In one embodiment, the body 309 and sealing layer 390 are placed onto a heated surface to ensure that the sealing layer 390 is sealed onto the surface of the bottom side 375 of the body 309. The heated surface can be a hot plate at a temperature within the range of from about 50° C. to about 160° C., from about 80° C. to about 120° C., or about 100° C. The sealing layer 390 and body 309 can be held on the heated surface for a time having a value within the range of from about 20 seconds to about ten minutes, from about 40 seconds to about five minutes, or for about one minute. Optionally, force is applied on the body 309 and sealing layer 390 assembly during the time that the assembly is on the heated surface.

The assembly is removed from the heated surface and, while still hot, any air pockets located between the sealing layer 390 and the body 309 are removed by, for example, pressing or rubbing the sealing layer 390, for example, with a block that is rubbed over the sealing layer 390. In one embodiment, any air pockets located between the sealing layer 390 and the surface of the bottom side 375 of the body 309 are removed. Prior to adding the sealing layer 390 to the surface of the bottom side 375 of the body 309, each channel of the cartridge 201 has a cross-section shaped substantially like the letter "C". Upon adhering the sealing layer 390 to the surface of the bottom side 375 of the body 309 the cross-section of each channel is shaped substantially like the letter "D".

The cartridge 201 also includes a tab 380 that a user can grasp, which allows a user to easily insert or remove the cartridge 201 from an instrument (e.g., the instrument of FIG. 2).

Figure 4:
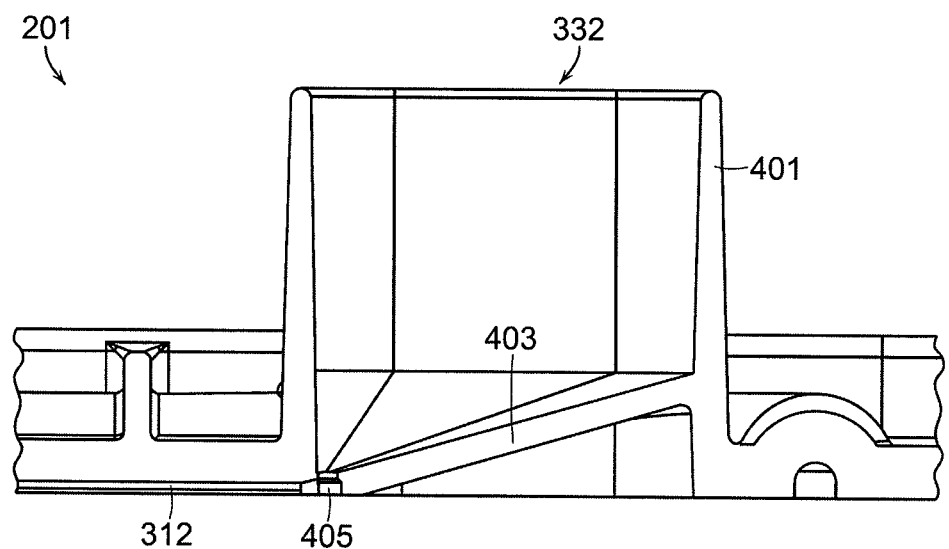
FIG. 4 is a cross-sectional side view of a fluid input of the cartridge of FIGS. 3A and 3B.

FIG. 4 is a cross-sectional side view of a fluid input 332 of the cartridge 201 of FIGS. 3A and 3B. The fluid input 332 has a wall 401 that extends from the surface of the top side 370 of the body 309 of the cartridge 201. In one embodiment, when the cartridge 210 is installed in the instrument (e.g., the instrument 210 of FIG. 2), the fluid inputs 332 remain outside and near a cover (e.g., the cover 190 of FIG. 1) enclosing the instrument (e.g., the instrument 210 of FIG. 2). The wall 401 of the fluid input 332 is shaped to provide a user with the ability to easily transfer a sample from a sample transfer device without interference from the cover (e.g., the cover 190 of FIG. 1) because the fluid input 332 is not obscured by other portions of the instrument (e.g., the instrument 210 of FIG. 2). In this embodiment, the wall 401 is ovate-shaped so that a user can position a pipette at an angle with respect to a horizontal axis of the system 200 and locate the pipette's tip within the wall 401 to deposit a sample without interference from the cover (e.g., the cover 190 of FIG. 1) enclosing the instrument (e.g., the instrument 210 of FIG. 2).

Each fluid input 332 has a sloped bottom portion 403 and an outlet 405. The bottom portion 403 directs a sample into the fluid input channel 312 via the outlet 405. In this embodiment, the aperture has a diameter of 0.05588 cm (0.022 in). In some embodiments the aperture of each fluid input 332 has a diameter between 0.0508 cm (0.020 in) and 0.254 cm (0.1 in). The sloping of the bottom portion 403 ensures that as little sample as possible is left behind in the fluid input 332 upon completion of the use of the system (i.e., minimizes dead volume). This embodiment of the fluid input 332 acts like a funnel so that most of a sample can be drawn from the fluid input 332 without drawing air into the cartridge and introducing bubbles into the cartridge. In this embodiment, the fluid input 332 has a capacity to hold about 400 microliters of a sample. In one embodiment, during operation of the cartridge 201, the fluid input channel 312 leading from the fluid input 332 is pre-primed with a buffer solution. The cartridge 201 is pre-primed, among other things, to remove gas slugs and bubbles and to establish and maintain a wetted path through the cartridge. In one embodiment, the fluid input channels 312 are pre-primed. For example, a buffer solution is drawn into the fluid reservoirs 342 from the common reagent input channel 317. Then, the buffer solution is pushed from the fluid reservoirs 342 into the fluid input channels 312.

Figure 5:
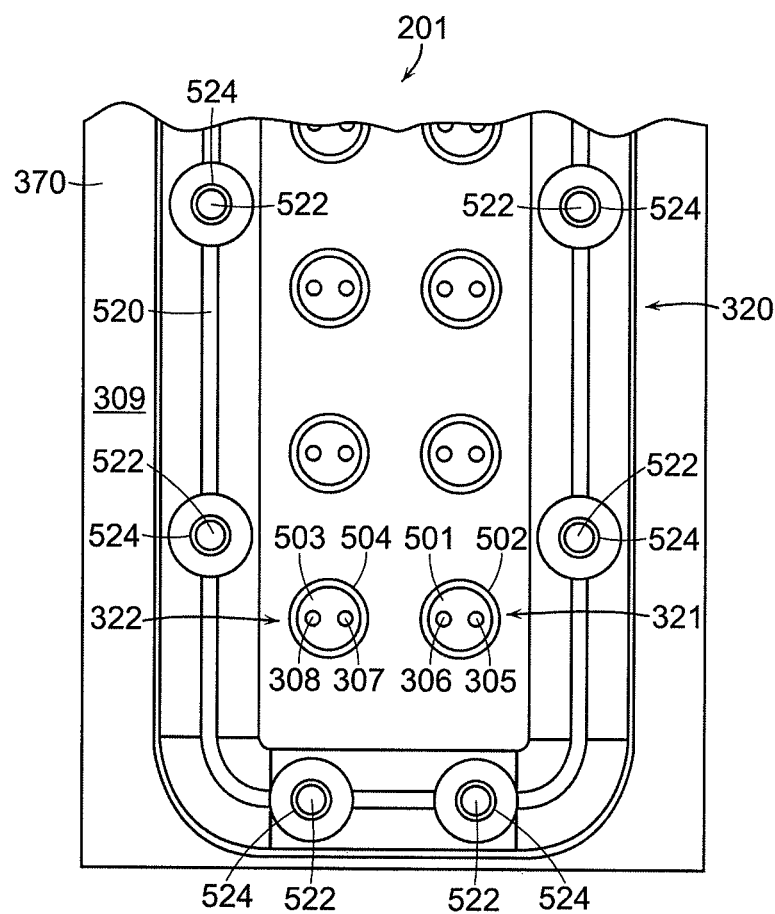
FIG. 5 is a top view of the output valve assembly of the cartridge of FIGS. 3A and 3B without a flexible sheet.
Figure 6:
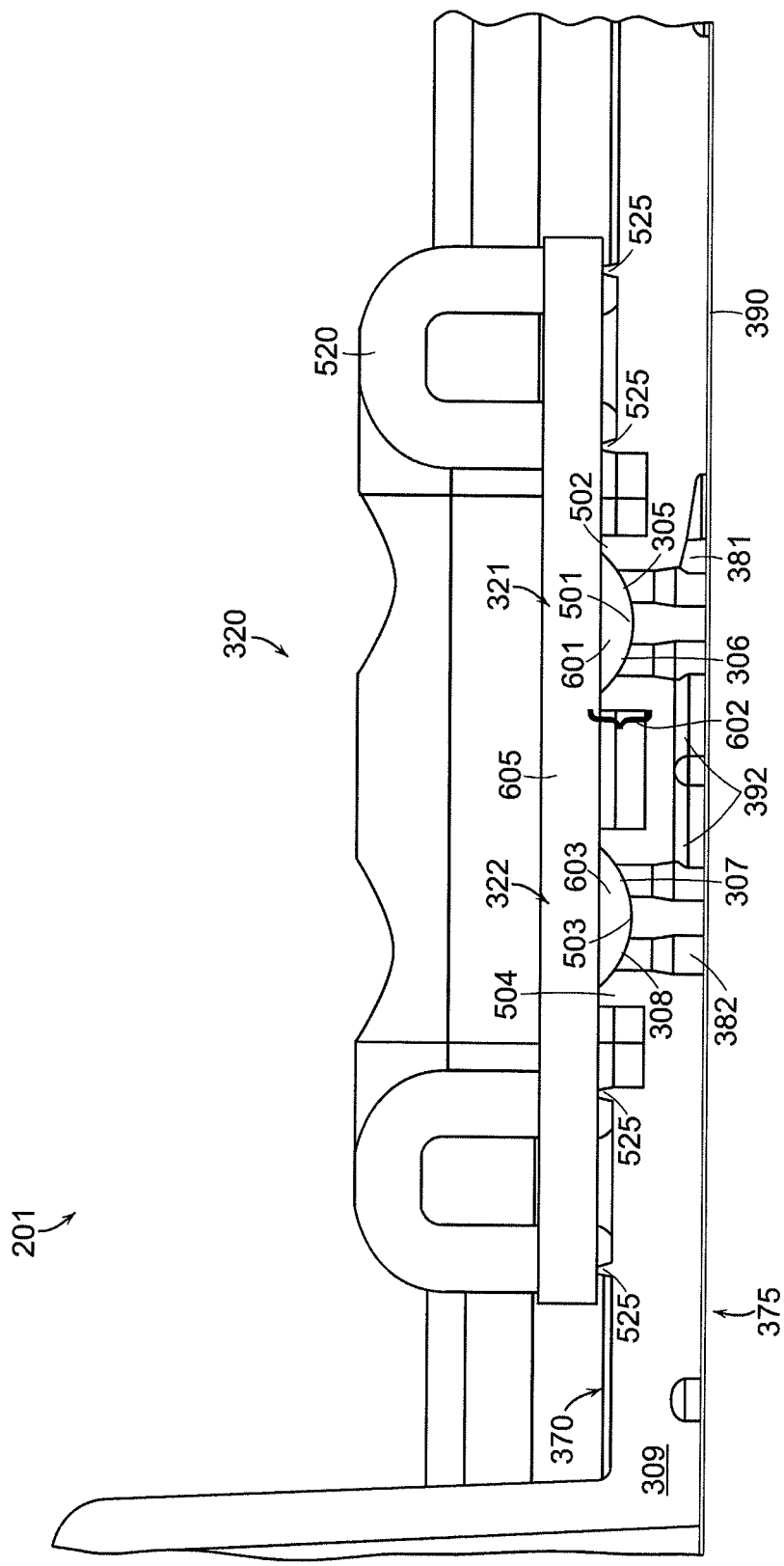
FIG. 6 is a cross-sectional side view of the output valve assembly of the cartridge of FIGS. 3A and 3B.

FIG. 5 is a top view of the output valve assembly 320 of the cartridge 201 of FIGS. 3A and 3B without a flexible sheet. FIG. 6 is a cross-sectional side view of the output valve assembly 320 of the cartridge 201 of FIGS. 3A and 3B with a flexible sheet 605. The output valve assembly 320 includes a first output valve 321 and a second output valve 322. The first output valve 321 is formed on the top side 370 of the body 309 and includes a first recess 501 and a first recess wall 502 surrounding the first recess 501. Each recess 501, 503 is in the shape of a bowl that is, for example, 0.0508 cm (0.020 in) deep with a 0.23368 cm (0.092 in) diameter. Referring to FIG. 6, in one embodiment, the first recess wall 502 is fabricated by forming a protrusion 602 extending away from the first side 370 of the body 309 and forming a recess 503 in the protrusion 602. The first recess wall 502 is adapted to mate with and seal against a flexible sheet 605 covering the first recess wall 502 and the first recess 501 when the cartridge 201 is inserted into an instrument (e.g., the instrument 210 of FIG. 2).

The first output valve 321 further includes a first aperture (e.g., the inlet 305 of FIG. 3B) and a second aperture (e.g., the outlet 306 of FIG. 3B). In some embodiments, the first and second apertures are either an inlet or an outlet depending on the direction that a fluid flows through the valve. As shown in FIG. 6, the first recess 501 is in fluid communication with the processing device output channel 381 on the bottom side 375 of the body 309 via the first aperture 305. Also, the first recess 501 is in fluid communication with the fluid reservoir channel 392 on the bottom side 375 of the body 309 via the second aperture 306.

The output valve assembly 320 further includes a valve assembly wall 520. The valve assembly wall 520 surrounds the first recess 501 and the first recess wall 502. The valve assembly wall 520 is also adapted to mate with and seal against a flexible sheet. In this embodiment, the valve assembly wall 520 is a retainer that includes apertures 524 that are configured to mate with complementary posts 522 that extend from the surface of the top side 370 of the cartridge 201. A flexible sheet 605 is placed between ridges 525 that extend from the top side 370 of the body 309 of the cartridge 201 and the valve assembly wall 520 is heat-staked to the complementary posts 522. In this way, the flexible sheet 605 is forced onto, and makes a perimeter seal with, the ridges 525.

The second output valve 322 is formed on the top side 370 of the body 309 and includes a second recess 503 and a second recess wall 504 surrounding the second recess 503. The second recess wall 504 is adapted to mate with and seal against a flexible sheet (e.g., the flexible sheet 605 shown in FIG. 6) covering the second recess wall 504 and the second recess 503 when the cartridge 201 is inserted into the sample processing system 200 (FIG. 2). In one embodiment, a surface on the movable head assembly 202 applies a force to a flexible sheet covering the second recess wall 504 and the second recess 503 so that the second recess wall 504 mates with and seals against the flexible sheet. The valve assembly wall 520 also surrounds the second recess 501 and the second recess wall 502.

The second output valve 322 further includes a first aperture (e.g., the inlet 307 of FIG. 3B) and a second aperture (e.g., the outlet 308 of FIG. 3B). As shown in FIG. 6, the second recess 503 is in fluid communication with the fluid reservoir channel 392 on the bottom side 375 of the body 309 via the first aperture 307. Also, the second recess 503 is in fluid communication with the waste output channel 382 on the bottom side 375 of the body 309 via the second aperture 308. In one embodiment, the first and second recess walls 502, 504 are raised about 0.0254 cm (0.010 in) with respect to the surface of the top side 370 of the body 309. In another embodiment, the first and second recess walls 502, 504 are raised 0.076 cm (0.030 in) above the surface immediately adjacent to the first and second recess walls 502, 504 (e.g., the height of protrusion 602). In another embodiment, the first and second recess walls 502, 504 have a 0.033 cm (0.013 in) flat width for making a seal with a flexible sheet 605 when the movable head assembly 202 applies a force to the flexible sheet. In another embodiment, the flexible sheet 605, about 0.0308 to 0.127 cm (0.020 to 0.050 in) thick, covers the recess 501, 503 and the recess wall 502, 504.

When a movable head assembly 202 applies a force to the top surface of the flexible sheet 605, the flexible sheet 605 seals against the top of the recess wall 502, 504, forming a sealed fluid chamber 601, 603 in each valve 321, 322. In one embodiment, the flexible sheet 605 is a silicone membrane. In another embodiment, the flexible sheet 605 is located on the surface of the top side 370 of the body 309, tensioned, and clamped prior to being heat-staked to the cartridge 201. As described above, the flexible sheet 605 is heat-staked to the top side 370 of the body 309 by using the valve assembly wall 520 and posts 522 that protrude from the body 309 of the cartridge 201 and mate with the valve assembly wall 520. In yet another embodiment, the movable head assembly 202 applies a force of about 6.67 N (1.5 lb) per each output valve 321, 322 to seal the output valves 321, 322.

The input valve assembly 310 is designed in a similar way as described above with respect to the output valve assembly 320. The reagent input valve 311 of the input valve assembly 310 is formed on the top side 370 of the body 309 and includes a first recess (e.g., the first recess 501 of FIG. 6) and a first recess wall (e.g., the first recess wall 502 of FIG. 6) surrounding the first recess (e.g., the first recess 501 of FIG. 6). In one embodiment, the first recess wall (e.g., the first recess wall 502 of FIG. 6) is fabricated by forming a protrusion (e.g., the protrusion 602 of FIG. 6) extending away from the first side 370 of the body 309 and forming a recess (e.g., the first recess 501 of FIG. 6) in the protrusion (e.g., the protrusion 602 of FIG. 6). The first recess wall (e.g., the first recess wall 502 of FIG. 6) is adapted to mate with and seal against a flexible sheet (e.g., the flexible sheet 605 of FIG. 6) covering the first recess wall (e.g., the first recess wall 502 of FIG. 6) and the first recess (e.g., the first recess 501 of FIG. 6) when the cartridge 201 is inserted into the sample processing system 200 (FIG. 2).

The reagent input valve 311 further includes a first aperture (e.g., the first aperture 305 of FIG. 6) and a second aperture (e.g., the second aperture 306 of FIG. 6). The first recess (e.g., the first recess 501 of FIG. 6) is in fluid communication with the reagent input channel 371 on the bottom side 375 of the body 309 via the first aperture (e.g., the first aperture 305 of FIG. 6). Also, the first recess (e.g., the first recess 501 of FIG. 6) is in fluid communication with the processing device input channel 313 on the bottom side 375 of the body 309 via the second aperture (e.g., the second aperture 306 of FIG. 6).

The input valve assembly 310 further includes a valve assembly wall (e.g., the valve assembly wall 520 of FIG. 6). The valve assembly wall (e.g., the valve assembly wall 520 of FIG. 6) surrounds the first recess (e.g., the first recess 501 of FIG. 6) and the first recess wall (e.g., the first recess wall 502 of FIG. 6). The valve assembly wall (e.g., the valve assembly wall 520 of FIG. 6) is also adapted to mate with and seal against a flexible sheet. In this embodiment, the valve assembly wall (e.g., the valve assembly wall 520 of FIG. 6) includes apertures (e.g., the apertures 524 of FIG. 6) that are configured to mate with complementary posts (e.g., the posts 522 of FIG. 6) that extend from the surface of the top side 370 of the cartridge 201. A flexible sheet is placed between the surface of the top side 370 of the cartridge 201 and the valve assembly wall (e.g., the valve assembly wall 520 of FIG. 6) and the valve assembly wall (e.g., the valve assembly wall 520 of FIG. 6) is heat-staked to the complementary posts (e.g., the posts 522 of FIG. 6). In this way, the flexible sheet (e.g., the flexible sheet 605 of FIG. 6) is heat-staked over the first recess (e.g., the first recess 501 of FIG. 6) and the first recess wall (e.g., the first recess wall 502 of FIG. 6).

The fluid input valve 312 is formed on the top side 370 of the body 309 and includes a second recess (e.g., the second recess 503 of FIG. 6) and a second recess wall (e.g., the second recess wall 504 of FIG. 6) surrounding the second recess (e.g., the second recess 503 of FIG. 6). The second recess wall (e.g., the second recess wall 504 of FIG. 6) is adapted to mate with and seal against a flexible sheet (e.g., the flexible sheet 605 of FIG. 6) covering the second recess wall (e.g., the second recess wall 504 of FIG. 6) and the second recess (e.g., the second recess 503 of FIG. 6) when the cartridge 201 is inserted into the sample processing system 200 (FIG. 2). In one embodiment, a surface on the movable head assembly 202 applies a force to a flexible sheet covering the second recess wall (e.g., the second recess wall 504 of FIG. 6) and the second recess (e.g., the second recess 503 of FIG. 6) so that the second recess wall (e.g., the second recess wall 504 of FIG. 6) mates with and seals against the flexible sheet to form a sealed chamber (e.g., the chamber 603 of FIG. 6). The valve assembly wall (e.g., the valve assembly wall 520 of FIG. 6) also surrounds the second recess (e.g., the first recess 501 of FIG. 6) and the second recess wall (e.g., the first recess wall 502 of FIG. 6).

The fluid input valve 312 further includes a first aperture (e.g., the first aperture 307 of FIG. 6) and a second aperture (e.g., the second aperture 308 of FIG. 6). The second recess (e.g., the second recess 503 of FIG. 6) is in fluid communication with the fluid input channel 372 on the bottom side 375 of the body 309 via the first aperture (e.g., the first aperture 307 of FIG. 6). Also, the second recess (e.g., the second recess 503 of FIG. 6) is in fluid communication with the processing device input channel 313 on the bottom side 375 of the body 309 via the second aperture (e.g., the second aperture 308 of FIG. 6).

In one embodiment, the first and second recess walls (e.g., the first and second recess walls 502, 504 of FIG. 6) are raised about 0.0254 cm (0.010 in) with respect to the surface of the top side 370 of the body 309. In another embodiment, the first and second recess walls 502, 504 are raised 0.076 cm (0.030 in) above the surface immediately adjacent to the first and second recess walls 502, 504 (e.g., the height of protrusion 602 of FIG. 6). In another embodiment, the first and second recess walls (e.g., the first and second recess walls 502, 504 of FIG. 6) have a 0.0254 cm (0.010 in) flat width for making a seal with a flexible sheet when the movable head assembly 202 applies a force to the flexible sheet. In another embodiment, a surface on the movable head assembly 202 applies a force to a flexible sheet covering the first and second recess walls (e.g., the first and second recess walls 502, 504 of FIG. 6) and the first and second recesses (e.g., the first and second recesses 501, 503 of FIG. 6) so that the first and second recess walls (e.g., the first and second recess walls 502, 504 of FIG. 6) mate with and seal against the flexible sheet. In yet another embodiment, the movable head assembly 202 applies a force of about 1.5 lb 6.67 N per each output valve 321, 322 to seal the output valves 321, 322.

Figure 7:
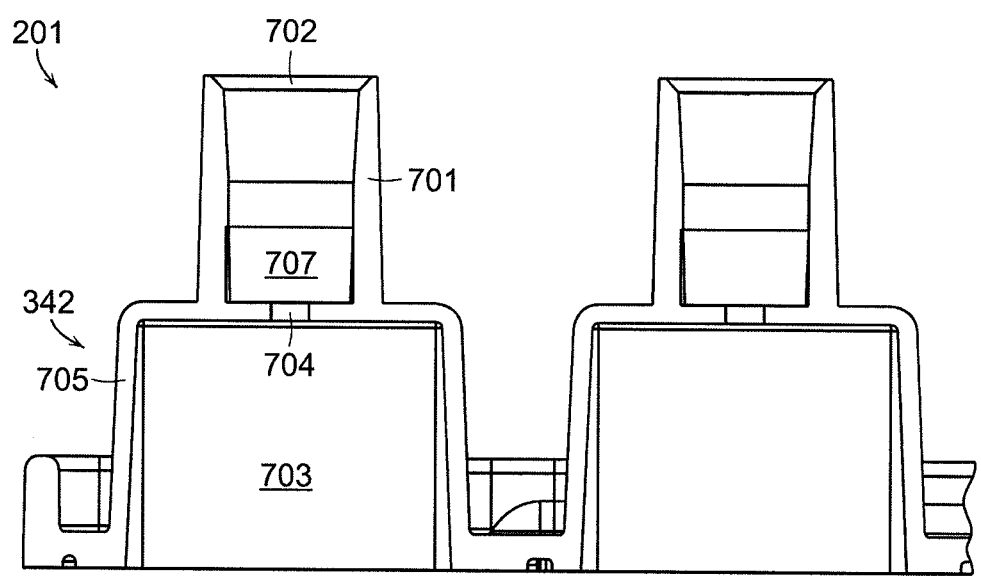
FIG. 7 is a cross-sectional side view of a reservoir of the cartridge of FIGS. 3A and 3B.

FIG. 7 is a cross-sectional side view of a fluid reservoir 342 of the cartridge 201 of FIGS. 3A and 3B. Each fluid reservoir 342 includes a chamber 703 that has an aperture 704 and a first wall 705. The chamber can be designed to hold any given volume of a sample. In one embodiment, the chamber 703 is sized to hold the total volume of a sample needed to execute an assay process. For example, the chamber 703 may have the capacity for about 1.2 ml of fluid. A second wall 701 surrounds the aperture 704 and extends from an exterior surface of the chamber 703. The second wall 701 is configured to align, mate, and seal with a pump interface member, similarly as described herein. In one embodiment, the interior surface of the second wall 701 mates with an exterior surface of a cylindrically-shaped pump interface member that is sized to fit within the second wall 701.

In some embodiments, the top surface 702 at the open end of the second wall 701 aligns, mates, and seals with a pump interface member. For example, referring to FIG. 14, the top surface 702 can mate and seal with the top portion 1444 of the pump interface member 1446 through o-ring 1445. In this embodiment, the bottom portion 1448 of the pump interface member 1446 has a conical shape and the top surface 702 of the second wall 701 is beveled. The conical shape of the pump interface member 1446 and the beveled top surface 702 of the second wall 701 allows the pump interface member 1446 to enter within the second wall 701 when the fluid reservoir 342 is misaligned with respect to the pump interface member 1446. In the case where the fluid reservoir 342 is misaligned with respect to the pump interface member 1446, as the pump interface member 1446 enters within the second wall 701, the top surface 702 of the second wall 701 touches and slides along the surface of the conically-shaped portion the pump interface member 1466 until the fluid reservoir 342 and the pump interface member 1466 align and mate with each other.

A gas permeable, liquid impermeable element 707 fits within the second wall 701 and sits on the top exterior surface of the chamber 703 over the aperture 704. In this embodiment, the element 707 prevents liquids and liquid vapors from entering and damaging an air control device that interfaces with the fluid reservoir 342. In other embodiments, the element 707 may be a membrane or a filter (e.g., a matrix filter).

Figure 8:
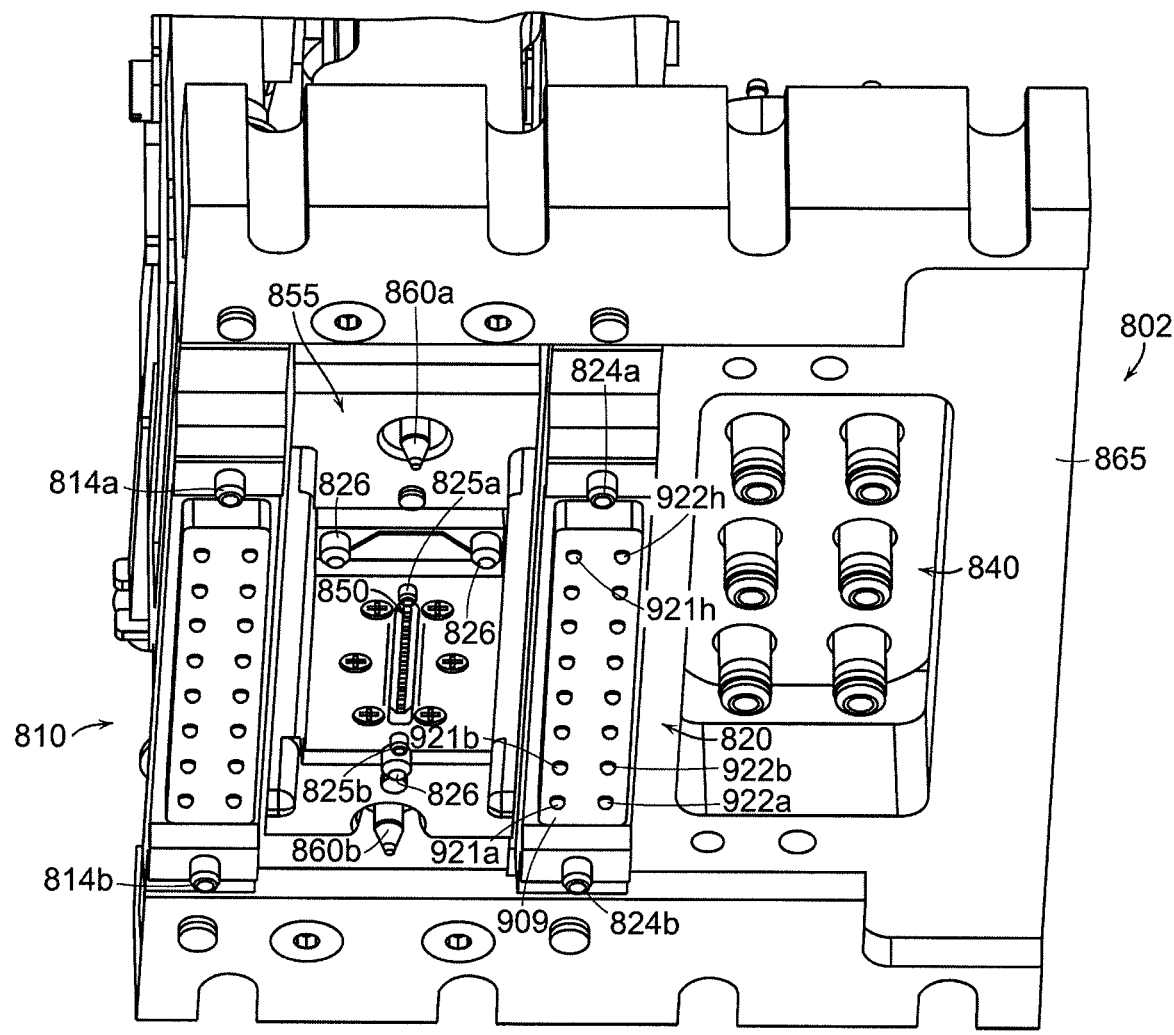
FIG. 8 is a perspective bottom view of a movable head assembly for use with a cartridge, according to an illustrative embodiment of the invention.

FIG. 8 is a perspective bottom view of a movable head assembly 802 for use with a cartridge (e.g., the cartridge 201 of FIGS. 3A and 3B). The movable head assembly 802 includes an input valve assembly interface 810 and an output valve assembly interface 820. The valve interfaces 810, 820 apply a force to the valve assemblies 110, 120 on the cartridge 201 to form a sealed fluid chamber in each of the valves of the valve assemblies 110, 120 (see, for example, FIG. 1).

The movable head assembly 802 also includes a processing device interface 850 and an air control device interface 840. The processing device interface 850 provides an electrical and/or magnetic interface to the processing device 350 to operate the processing device 350 and to communicate with the processing device 350. The pump interface 840 interfaces with the fluid reservoirs 342 and provides air displacement force to move fluid through the cartridge 201.

As previously described, the cartridge 201 includes both coarse positioning members (e.g., 360a, 360b of FIG. 3A) and fine positioning apertures (e.g., 314a, 314b, 324a, 324b, 325a, 325b, 326a, 326b of FIGS. 3A and 3B) to properly position the movable head assembly 202 and its components with respect to the cartridge 201 and its components. As shown in FIG. 8, the movable head assembly 802 includes two coarse positioning pins 860a, 860b attached to the movable head assembly's base 865 that are designed to fit within the walls of the two coarse positioning members 360a, 360b of the cartridge 201 (FIG. 3A). The two coarse positioning pins 860a, 860b have conical-shaped tips to ensure that they properly locate the two corresponding coarse positioning members 360a, 360b of the cartridge 201 (FIG. 3A).

Each of the interfaces 810, 820, 840, and 855 of the movable head assembly 202 include positioning pins to finely align each of the interfaces with a corresponding device on the cartridge 201. For example, the input valve assembly interface 810 features positioning pins 814a, 814b that mate and align with the corresponding input valve assembly positioning apertures 314a, 314b of the cartridge 201 (FIG. 3A). Likewise, the output valve assembly interface 820 features positioning pins 824a, 824b that mate and align with the corresponding output valve assembly positioning apertures 324a, 324b of the cartridge 201. As illustrated in FIG. 8, the tips of the positioning pins 814a, 814b, 824a, 824b are shaped to ensure that the valve assembly interfaces 810, 820 properly locate and guide the positioning pins 814a, 814b, 824a, 824b into the corresponding valve assembly apertures 314a, 314b, 324a, 324b in the cartridge 201. The processing device interface 855 also includes positioning pins 825a, 825b. The processing device positioning pins 825a, 825b, mate with the corresponding processing device positioning apertures on a cartridge (e.g., the positioning apertures 325a, 325b on the cartridge 201 of FIG. 3B). The processing device interface 855 also includes positioning members 826 for setting and maintaining a precise distance between the processing device interface 855 and a process device on a cartridge (e.g., the processing device 850 on the cartridge 201 of FIG. 3B).

Figure 9:
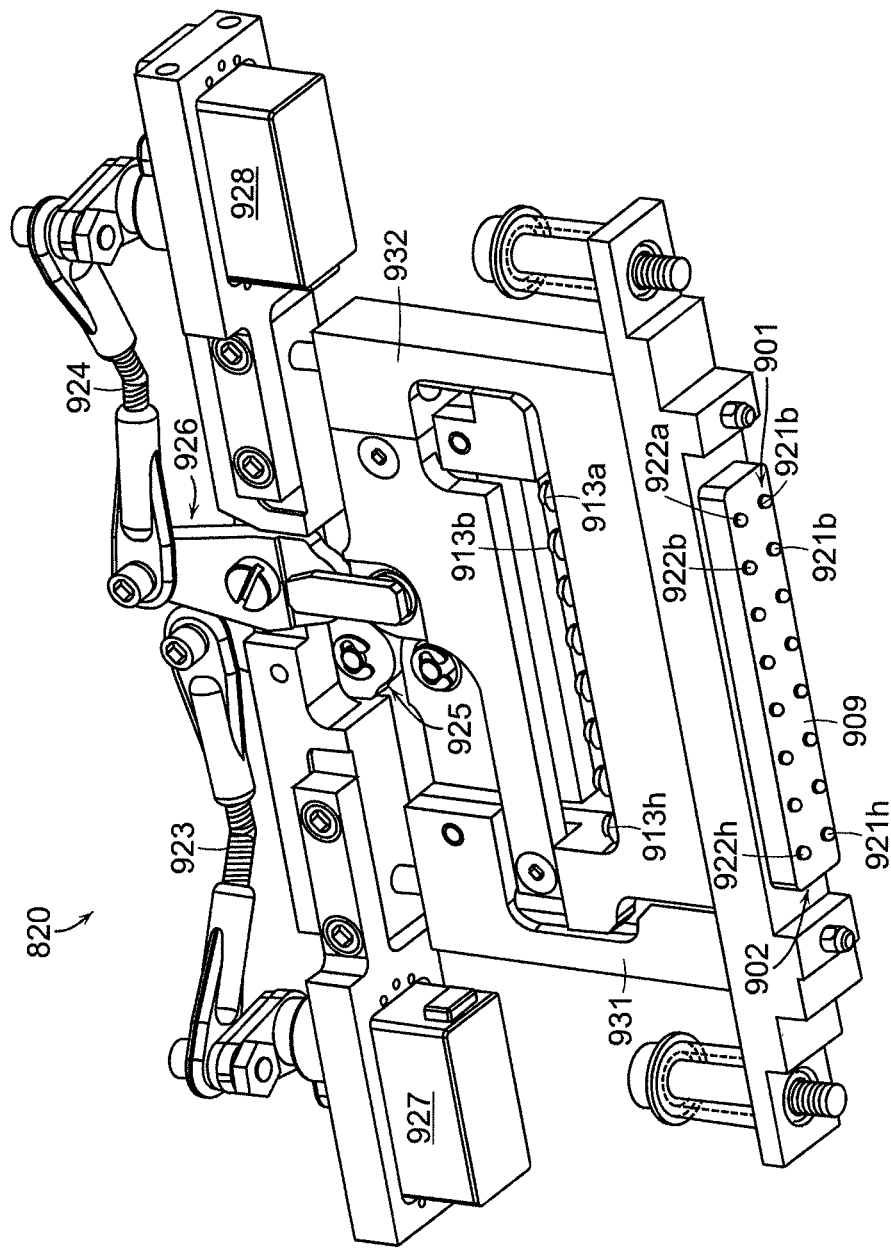
FIG. 9 is a perspective view of a valve actuator assembly of the movable head assembly of FIG. 8.

FIG. 9 is a perspective view of an embodiment of the valve actuator assembly 820 of the movable head assembly 802 of FIG. 8. The valve actuator assembly 820 includes a face seal element 909 that applies a force to a flexible sheet of a valve assembly on a cartridge when the movable head assembly engages with the cartridge. The applied force seals each of the valves in the valve assembly. For example, referring to FIG. 6, the face seal element 909 applies a force to the flexible sheet 605 of the output valve assembly 320 to seal the output valves 121, 122 when the movable head assembly 802 engages with the cartridge 201. In another embodiment, the valve actuator assembly 820 is separately movable and engages with the valve assembly in the cartridge 201 when the valve actuator assembly 820 is driven by a motor.

The valve actuator assembly 820 includes a row of first valve pins 921a-921h (generally, 921) of a first portion of the valve actuator assembly 931 and a row of second valve pins 922a-922h (generally, 922) of the second portion of the valve actuator assembly 931. The valve pins 921, 922 are positioned through apertures in the face seal 909. In one embodiment, the valve pins 921, 922 are about 0.15875 cm (0.0625 in) in diameter. Each valve pin 921 is individually sprung with a corresponding valve pin spring 913a-913h. The valve pin springs 913a-913h are selected to provide in the range of 2.22 to 4.45 N (0.5 to 1 lb) of sealing force. In the embodiment shown in FIG. 9, the valve actuator assembly 820 also includes a first motor 927, a first link arm 923, and a first bell crank 925, for synchronously driving the first valve pins 921. The valve actuator assembly 820 also includes a second motor 928, a second link arm 923, and a second bell crank 925, for driving the second valve pins 922. In one embodiment, the valve pins are driven asynchronously if a user desires to perform different analyses in different channels of the cartridge. In another embodiment, the valve actuator assembly 820 includes a plurality of motors, each of which drives a single valve pin 921, 922.

Figure 10:
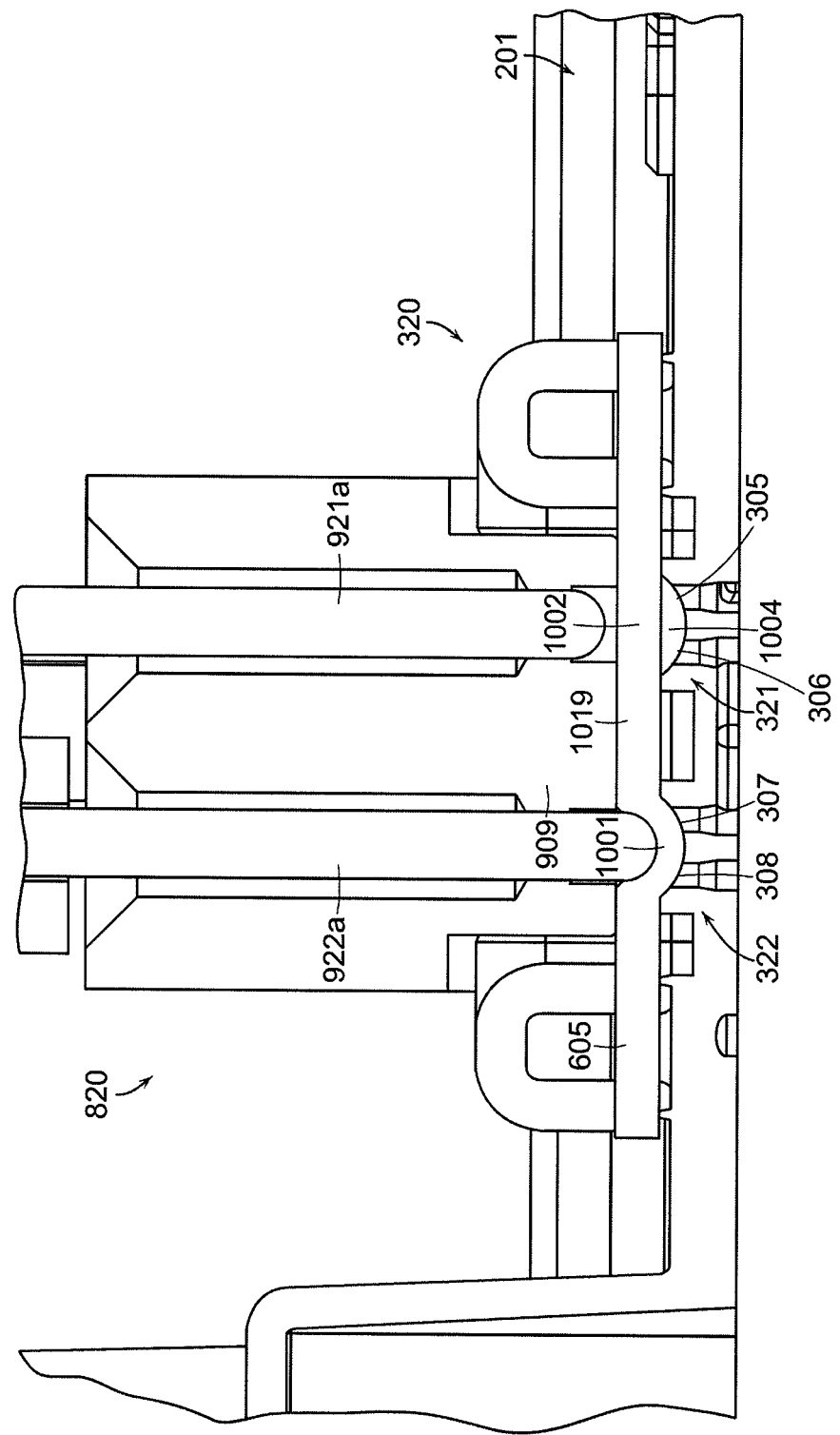
FIG. 10 is a cross-sectional side view of the valve actuator assembly of FIG. 9 mating with the output valve assembly of FIG. 6.

FIG. 10 is a cross-sectional side view of the valve actuator assembly 820 of FIG. 9 mating with the output valve assembly 320 of FIG. 6. As shown in FIG. 10, the valve actuator assembly 820 applies a force across the middle portion 1019 of the flexible sheet 605 to seal, for example, output valve 321 and to create a sealed fluid chamber 1004. In response to a command signal to close the second output valve 322, the second motor 928 drives valve pin 922a into a first portion 1001 of the flexible sheet 605 such that the first portion 1001 of the flexible sheet 605 covers and seals the aperture 307 and the aperture 308 of the second output valve 322. As a result, fluid cannot flow between the aperture 307 and the aperture 308 of the second valve 322.

In response to a command signal to open the first output valve 321, the first motor 927 moves to a predetermined release position (i.e., electrical current can be turned off when the first motor 927 reaches this position), the valve actuator assembly 931 retracts, and the force of the valve pin spring drives the valve pin 921a away from the flexible sheet 605. As a result, the second portion 1002 of the flexible sheet 605 does not cover and seal the apertures 305, 306 and fluid may flow between the apertures 305, 306 of the first output valve 321. In some embodiments, the second motor 928 moves to a predetermined engaged position in response to a command signal to close the second output valve 322, and valve pin spring 913 applies a force to drive the second valve pin 922 into the flexible sheet 605 and seal the aperture 307 and aperture 308 of the second output valve 322. In this embodiment, the motor current is turned off once the motor reaches the predetermined engaged position while the valve pins 922 remain engaged. Conversely, in response to a command signal to open the second output valve 322, the second motor 928 turns on and retracts the second valve pin 922. The silicone sheet 605 then recovers to its original position, out of the recess, and flow between the aperture 307 and aperture 308 resumes.

In this embodiment, the valve pins 921a, 921b have rounded tips. In other embodiments, the valve pins 921a, 921b have a different shaped tip. In one embodiment, the valve pins 921a, 921b have a conical shaped tip and a valve recess (e.g., the valve recess 502 of FIG. 5 and FIG. 6) is shaped to have a complementary shape to the tip of the valve pins 921a, 921b.

Figure 11:
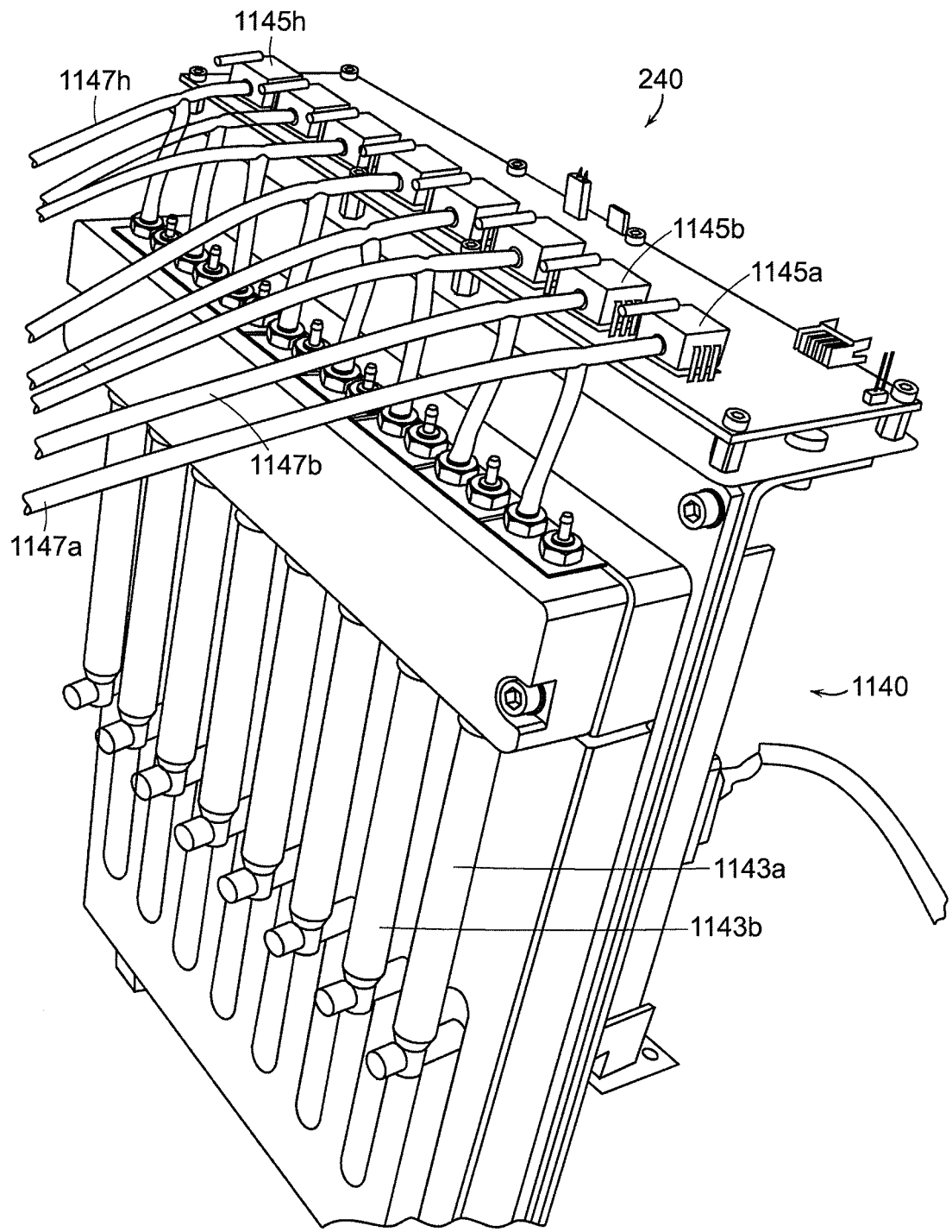
FIG. 11 is a perspective side view of the syringe pump assembly of FIG. 2.

FIG. 11 is a perspective side view of a syringe pump assembly 240 of the system 200 of FIG. 2. The syringe pump assembly 240 includes a syringe pump 1140 having eight syringes 1143a-1143h, eight pressure sensors 1145a-1145h, and eight tubes 1147a-1147h. In this embodiment, the syringe pump 1140 is a Tecan Cavro XMP 6008 Eight channel syringe pump (Tecan Trading AG, Switzerland). In other embodiments, other commercially available syringe pumps or custom fabricated syringe pumps can be used. Each pressure sensor 1145a-1145h senses pressure in each corresponding tube 1147a-1147h to detect leaks and observe proper function of the syringe pump 1140. In this embodiment, the pressure sensors are Honeywell SDX05D4 +/−5 V unamplified differential pressure sensors (Honeywell International Inc., Morristown, N.J.).

Figure 12A:
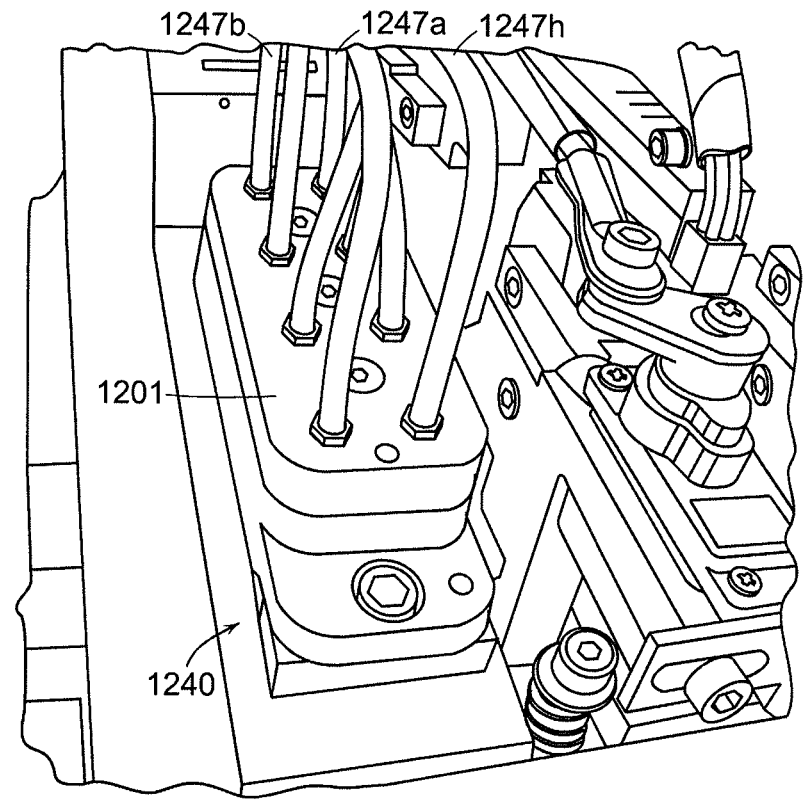
FIG. 12A is a perspective top view of a syringe pump interface assembly installed in an analyte processing system, according to an illustrative embodiment of the invention.
Figure 12B:
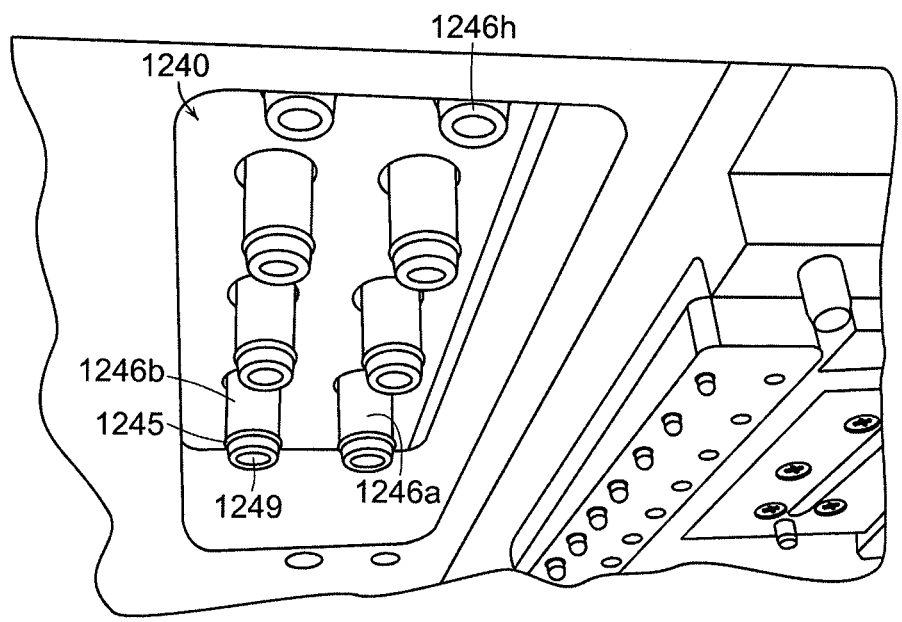
FIG. 12B is a perspective bottom view of the syringe pump interface assembly of FIG. 12A.
Figure 13:
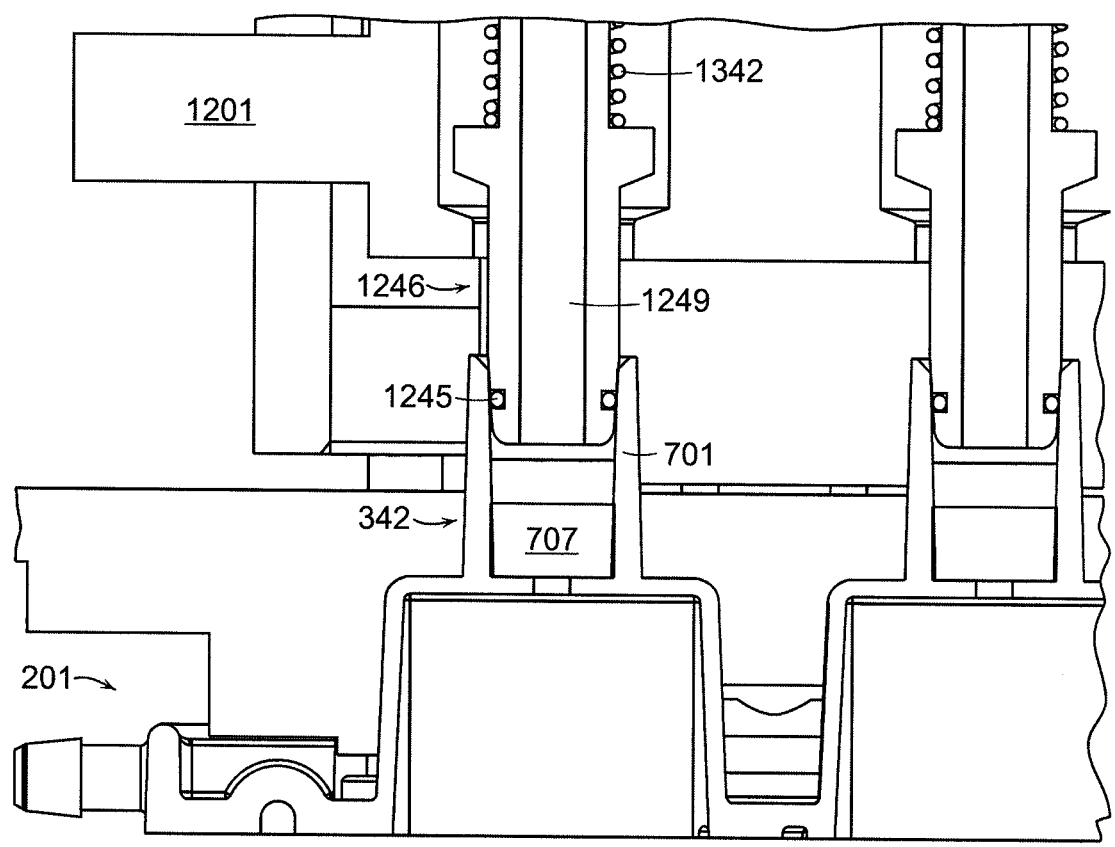
FIG. 13 is a cross-sectional side view of pump interface members of an instrument head mating with reservoirs of a cartridge, according to an illustrative embodiment of the invention.

FIG. 12A is a perspective top view of a syringe pump interface assembly 1240 installed in an analyte processing system, according to an illustrative embodiment of the invention. FIG. 12B is a perspective bottom view of the syringe pump interface assembly 1240 of FIG. 12A. Tubes 1247a-1247h (generally, 1247) from syringes on a syringe pump (e.g., the syringes of FIG. 11) 1143a-1143h connect to corresponding pump interface members 1246a-1246h through a syringe pump interface block 1201 of the syringe pump interface assembly 1240. In this embodiment, each pump interface member 1246 is fitted with an o-ring 1245, which provides a seal between the pump interface member 1246 and the inner surface of the second wall 701 of the fluid reservoir 342 as shown in FIG. 13. FIG. 13 is a cross-sectional side view of pump interface members 1246 of an instrument head (e.g., moveable head assembly 202 of FIG. 2) mating with fluid reservoirs 342 of the cartridge 201, according to an illustrative embodiment of the invention. The pump interface member 1246 has an aperture 1249 which is in fluid communication with the tube 1244. The aperture 1249 provides an air displacement force to the fluid reservoir 342 to draw or push fluid through the cartridge 201.

The pump interface member 1246 is spring-loaded to facilitate the alignment of the pump interface member 1246 with the second wall 701 of the fluid reservoir 342 when the instrument head engages with the cartridge. Specifically, each pump interface member 1246 is sprung with a spring 1342 to provide each pump interface member 1246 with the ability to self-align with the second wall 701 of the fluid reservoir 342. Embodiments of the pump interface members 1246 and the fluid reservoirs 342 are designed to reliably seal the air pump interface to the cartridge 201 over a variety of cartridge batches.

Figure 14:
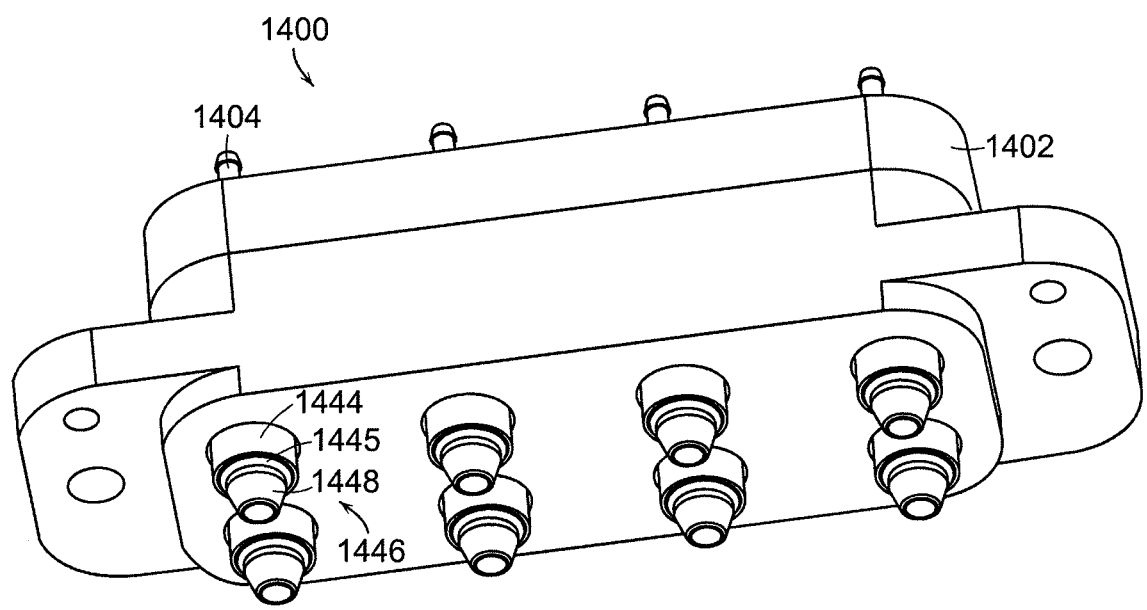
FIG. 14 is a perspective view of a syringe pump interface assembly, according to an illustrative embodiment of the invention.

FIG. 14 shows another embodiment of a pump interface assembly 1400. The pump interface assembly 1400 includes a block 1402 that houses multiple pump interface assembly members 1446. Each pump interface assembly member 1446 mates with and seals against a top surface (e.g., the top surface 702 of FIG. 7) of a second wall (e.g., the second wall 701 of FIG. 7) of a fluid reservoir (e.g., the fluid reservoir 342 of FIG. 3A) via an o-ring 1445 when the movable head assembly (e.g., the movable head assembly 202 of FIG. 2) engages with the cartridge (e.g., the cartridge 201 of FIG. 3A). The pump interface assembly 1400 also includes a plurality of barbs 1404 attached to the block 1408 and in fluid communication with corresponding pump interface members 1446. An air displacement pump can connect to the pump interface assembly 1400 through tubing attached to the barbs 1404.

Figure 15:
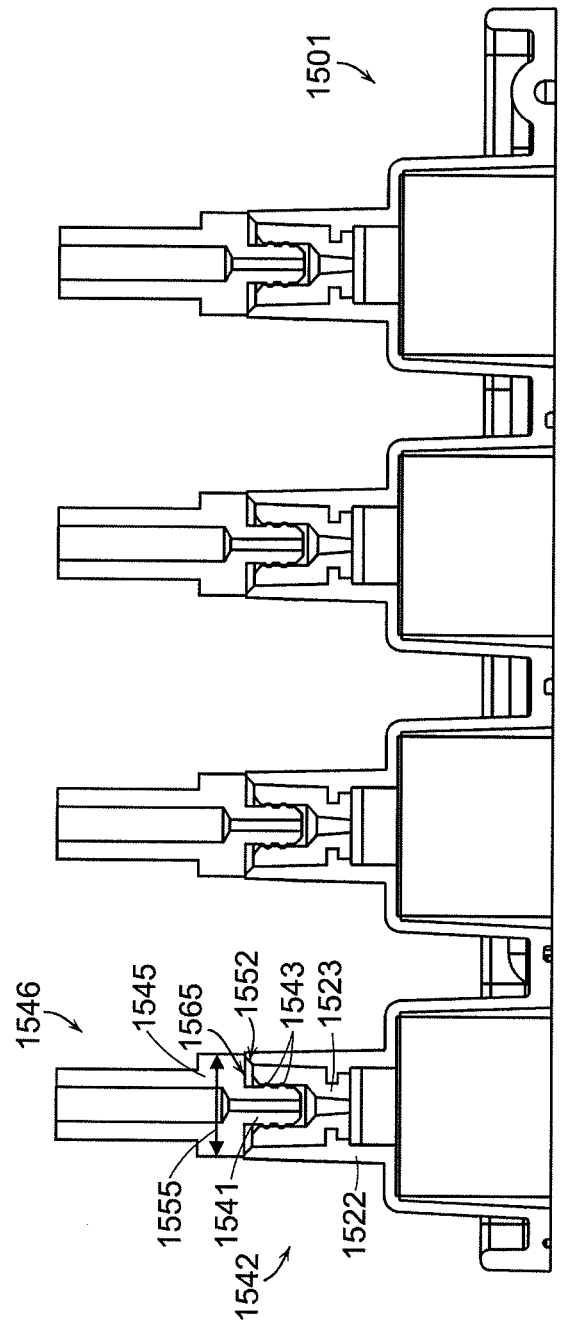
FIG. 15 is a cross-sectional side view of a plurality of pump interface members of an instrument head mating with a plurality of reservoirs of a cartridge, according to an illustrative embodiment of the invention.

FIG. 15 is a cross-sectional side view of a plurality of pump interface members 1546 of an instrument (e.g., the instrument 210 of FIG. 2) mating with a plurality of fluid reservoirs 1542 of a cartridge 1501, according to an illustrative embodiment of the invention. The pump interface member 1546 has a body portion 1545. The pump interface member 1546 also has a head portion 1541 with a smaller diameter than the body portion 1545 that extends from the top of the body portion 1545. The head portion 1541 mates with a sleeve 1523 lining the interior surface of the wall 1522. In this embodiment, the sleeve is made of a soft elastomeric material. In some embodiments, the sleeve is made of silicone, ethylene propylene diene monomer (EPDM), or thermoplastic elastomer (TPE) (e.g., Santroprene). The pump interface member 1546 has a body portion 1545 with a sufficiently large diameter 1555 so that the top surface 1565 of the body portion 1545 mates with the top surface 1552 of the wall 1522. The seal is formed between the outer surface of the head portion 1541 and the inner surface of the sleeve 1523. In this embodiment, there are ribs 1543 on the head portion 1541 that form a seal with the inside surface of the sleeve 1523.

Figure 16A:
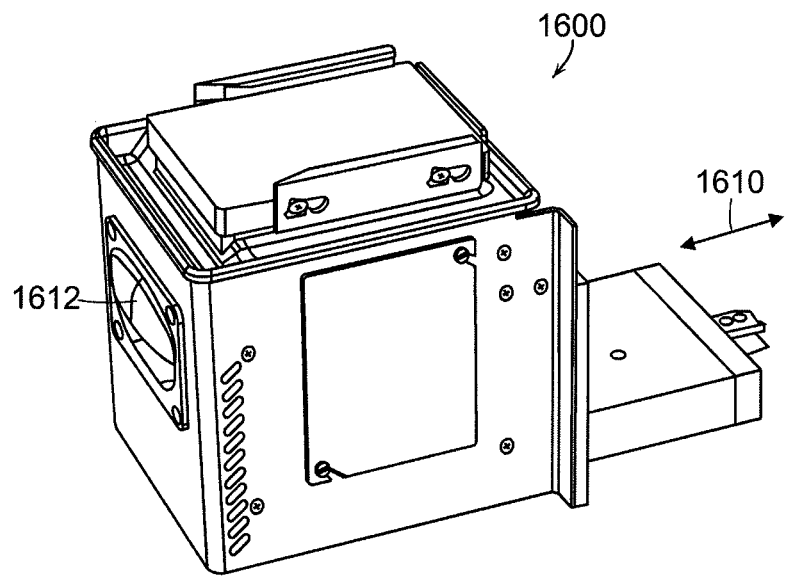
FIG. 16A is a perspective view of a plate assembly of a system for processing a sample that is configured to move toward and away from the system to facilitate easy loading of the cartridge and cleaning of a plate of the plate assembly, according to an illustrative embodiment of the invention.
Figure 16B:
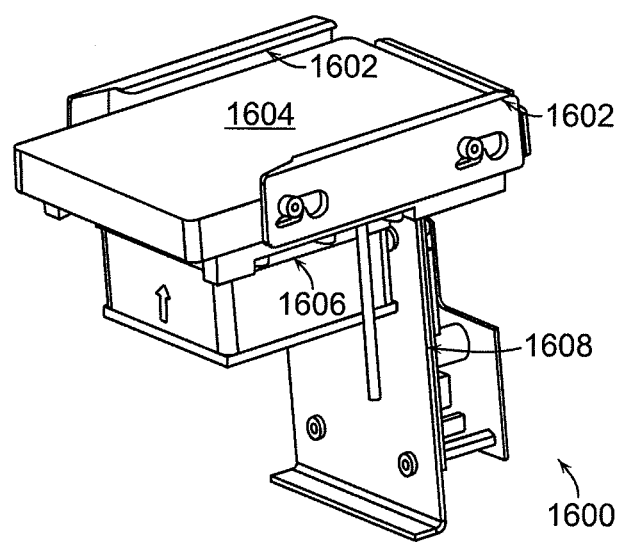
FIG. 16B is a perspective view of a portion of the plate assembly of FIG. 16A.

FIGS. 16A and 16B are perspective views of a plate assembly 1600 of an analyte processing system that is configured to move toward and away from the system to facilitate easy loading of the cartridge and cleaning of a plate 1604 of the plate assembly 1600 according to an illustrative embodiment of the invention. The plate assembly 1600 includes rails 1602, a plate 1604, temperature control devices 1606, electronics 1608, and a handle 1612. The plate assembly 1600 is designed to operate like a drawer that moves along a horizontal axis 1610 on a track attached to the base of an analyte processing system. The handle 1612 allows a user to pull the movable plate assembly 1600 away from the analyte processing system for easy loading of the cartridge (e.g., cartridge 201 of FIG. 2) and cleaning of the plate 1604 (e.g., similarly as described with respect to 103, 105 of FIG. 1). In another embodiment, a motor drives the movable plate assembly 1600 to specified locations with respect to the base of the analyte processing system in response to commands from a user.

The temperature control devices 1606 include a thermo electric cooling device and a fan to maintain a given cool temperature in the plate 1604. In other embodiments, the temperature control devices 1606 include both heating and cooling elements to maintain or change temperatures. The rails 1602 guide a cartridge (e.g., the cartridge 201 of FIG. 2) into position when a user manually installs the cartridge. In one embodiment, once the cartridge is affixed in position on the plate 1604, a movable head assembly (e.g., the moveable head assembly 202 of FIG. 2) automatically engages with the cartridge. The movable head assembly forces the cartridge against the surface of the plate 1604.

Figure 17:
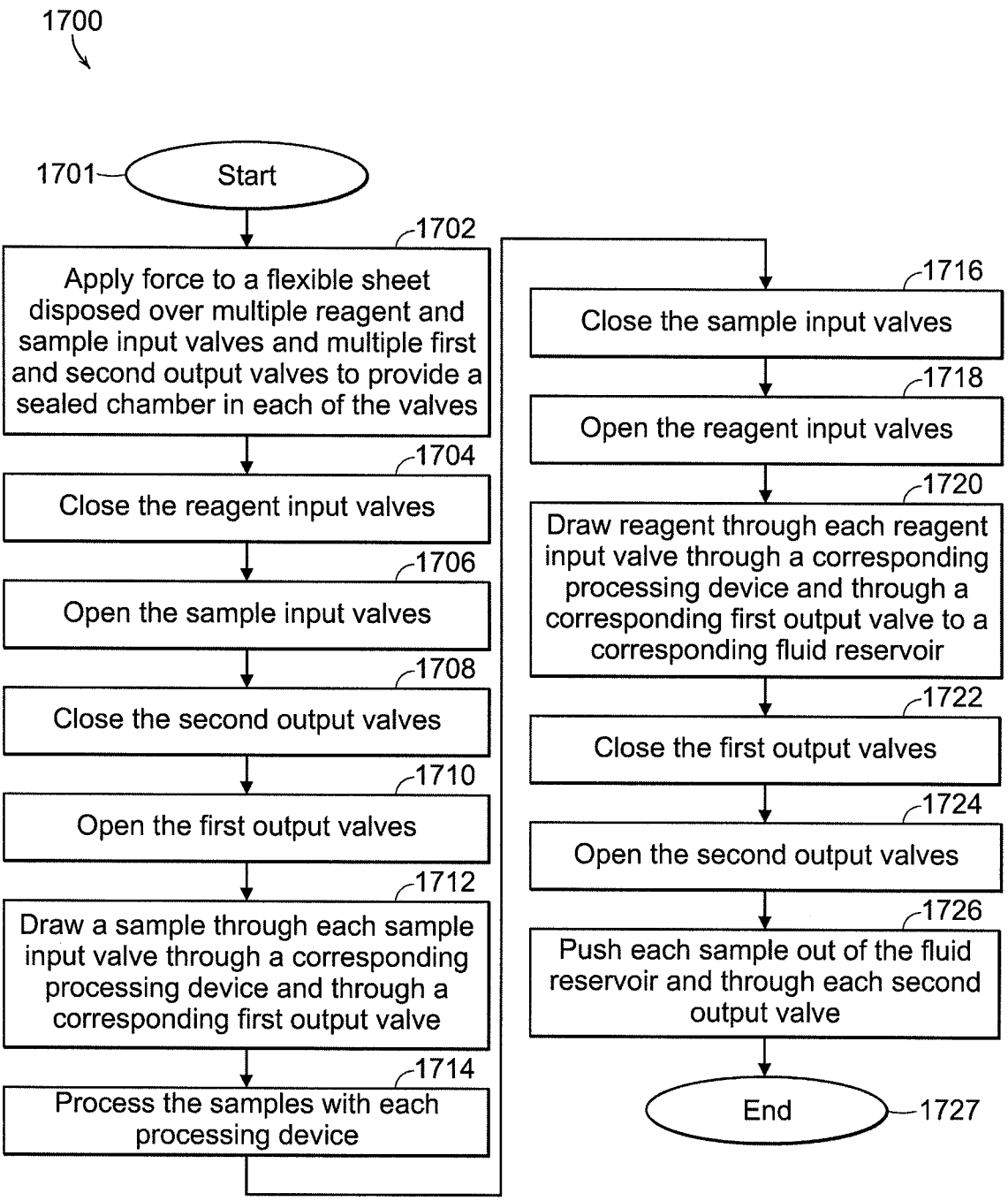
FIG. 17 is a flow diagram of a method of controlling a cartridge, according to an illustrative embodiment of the invention.

FIG. 17 is a flow diagram illustrating a method of operating a cartridge, according to an illustrative embodiment of the invention. After starting 1701, a force is applied to a flexible sheet (e.g., the flexible sheet 605 of FIG. 10) 1702 disposed over multiple reagent input valves (e.g., the reagent input valves 311 of FIG. 3A), fluid input valves (e.g., the fluid input valves 312 of FIG. 3A), first output valves (e.g., the first output valves 321 of FIG. 3A), and second output valves (e.g., the second output valves 322 of FIG. 3A) to provide a sealed chamber (e.g., the sealed fluid chamber 1004 of FIG. 10) in each of the input and output valves. Next, the reagent input valves (e.g., the reagent input valves 311 of FIG. 3A) are closed 1704 and the second output valves (e.g., the second output valves 322 of FIG. 3A) are closed 1708 (e.g., a valve pin is driven into a first portion 1001 of the flexible sheet 605 as shown in FIG. 10). Also, the fluid input valves (e.g., the fluid input valves 312 of FIG. 3A) are opened 1706 and the first output valves (e.g., the first output valves 321 of FIG. 3A) are opened 1710 (e.g., a valve pin is retracted away from a second portion 1002 of the flexible sheet 605 as shown in FIG. 10). Next, a sample (e.g., a sample from the fluid input 332 of FIG. 3A) is drawn through each fluid input valve (e.g., the fluid input valves 312 of FIG. 3A) through a corresponding processing device (e.g., the processing devices 351 of FIG. 3A) and through a corresponding first output valve (e.g., the first output valves 321 of FIG. 3A) 1712. The samples are then processed by each processing device (e.g., the processing devices 351 of FIG. 3A) 1714.

After the samples are processed 1714, the fluid input valves (e.g., the fluid input valves 312 of FIG. 3A) are closed 1716 (e.g., a valve pin is driven into a first portion 1001 of the flexible sheet 605 as shown in FIG. 10) and the reagent input valves are opened 1718 (e.g., a valve pin is retracted away from a second portion 1002 of the flexible sheet 605 as shown in FIG. 10). Next, a reagent is drawn through (1) each reagent input valve (e.g., the reagent input valves 311 of FIG. 3A), (2) a corresponding processing device (e.g., the processing devices 351 of FIG. 3A), and (3) a corresponding first output valve (e.g., the first output valves 321 of FIG. 3A) 1720. The flow of the reagent causes each of the samples to enter a corresponding fluid reservoir (e.g., the fluid reservoirs 342 of FIG. 3A). Next, the first output valves (e.g., the first output valves 321 of FIG. 3A) are closed (e.g., a valve pin is driven into a first portion 1001 of the flexible sheet 605 as shown in FIG. 10) 1722 and the second output valves (e.g., the second output valves 322 of FIG. 3A) are opened (e.g., a valve pin is retracted away from a second portion 1002 of the flexible sheet 605 as shown in FIG. 10) 1724. Before ending 1727, each sample is pushed out of each fluid reservoir (e.g., the fluid reservoirs 342 of FIG. 3A) and through each second output valve (e.g., the second output valves 322 of FIG. 3A) 1726. In another embodiment, the steps related to drawing fluid through a cartridge may be repeated many times before the step related to pushing fluid from the fluid reservoirs (e.g., the fluid reservoirs 342 of FIG. 3A) is executed.

In another embodiment, a dry cartridge (e.g., the cartridge 201 of FIG. 3A) is installed in the instrument (e.g., the instrument 210 of FIG. 2). First, the fluid input valves (e.g., the fluid input valves 312 of FIG. 3A) are closed (e.g., a valve pin is driven into a first portion 1001 of the flexible sheet 605 as shown in FIG. 10) and the reagent input valves are opened (e.g., a valve pin is retracted away from a second portion 1002 of the flexible sheet 605 as shown in FIG. 10). Next, a reagent is drawn through (1) each reagent input valve (e.g., the reagent input valves 311 of FIG. 3A), (2) a corresponding processing device (e.g., the processing devices 351 of FIG. 3A), and (3) a corresponding first output valve (e.g., the first output valves 321 of FIG. 3A). Next, the first output valves (e.g., the first output valves 321 of FIG. 3A) are closed (e.g., a valve pin is driven into a first portion 1001 of the flexible sheet 605 as shown in FIG. 10) and the second output valves (e.g., the second output valves 322 of FIG. 3A) are opened (e.g., a valve pin is retracted away from a second portion 1002 of the flexible sheet 605 as shown in FIG. 10).

Next, the fluid input valves (e.g., the fluid input valves 312 of FIG. 3A) are opened (e.g., a valve pin is retracted away from a second portion 1002 of the flexible sheet 605 as shown in FIG. 10), the reagent input valves are closed (e.g., a valve pin is driven into a first portion 1001 of the flexible sheet 605 as shown in FIG. 10), and the fluid inputs (e.g., the fluid inputs 332 of FIG. 3A) are filled with a reagent (e.g., a buffer solution). Next, the reagent is drawn through (1) each fluid input valve (e.g., the fluid input valves 312 of FIG. 3A), (2) a corresponding processing device (e.g., the processing devices 351 of FIG. 3A), and (3) a corresponding first output valve (e.g., the first output valve 321 of FIG. 3A). Next, the first output valves (e.g., the first output valves 321 of FIG. 3A) are closed (e.g., a valve pin is driven into a first portion 1001 of the flexible sheet 605 as shown in FIG. 10) and the second output valves (e.g., the second output valves 322 of FIG. 3A) are opened (e.g., a valve pin is retracted away from a second portion 1002 of the flexible sheet 605 as shown in FIG. 10). Before ending, the reagent is pushed out of each fluid reservoir (e.g., the fluid reservoirs 342 of FIG. 3A) and through each second output valve (e.g., the second output valves 322 of FIG. 3A). In this way, all channels of the cartridge (e.g., the cartridge 201 of FIG. 3B) are primed. Once all the channels are primed, the fluid inputs (e.g., the fluid inputs 332 of FIG. 3A) are filled with a sample and process 1700 starts.

Figure 18A:
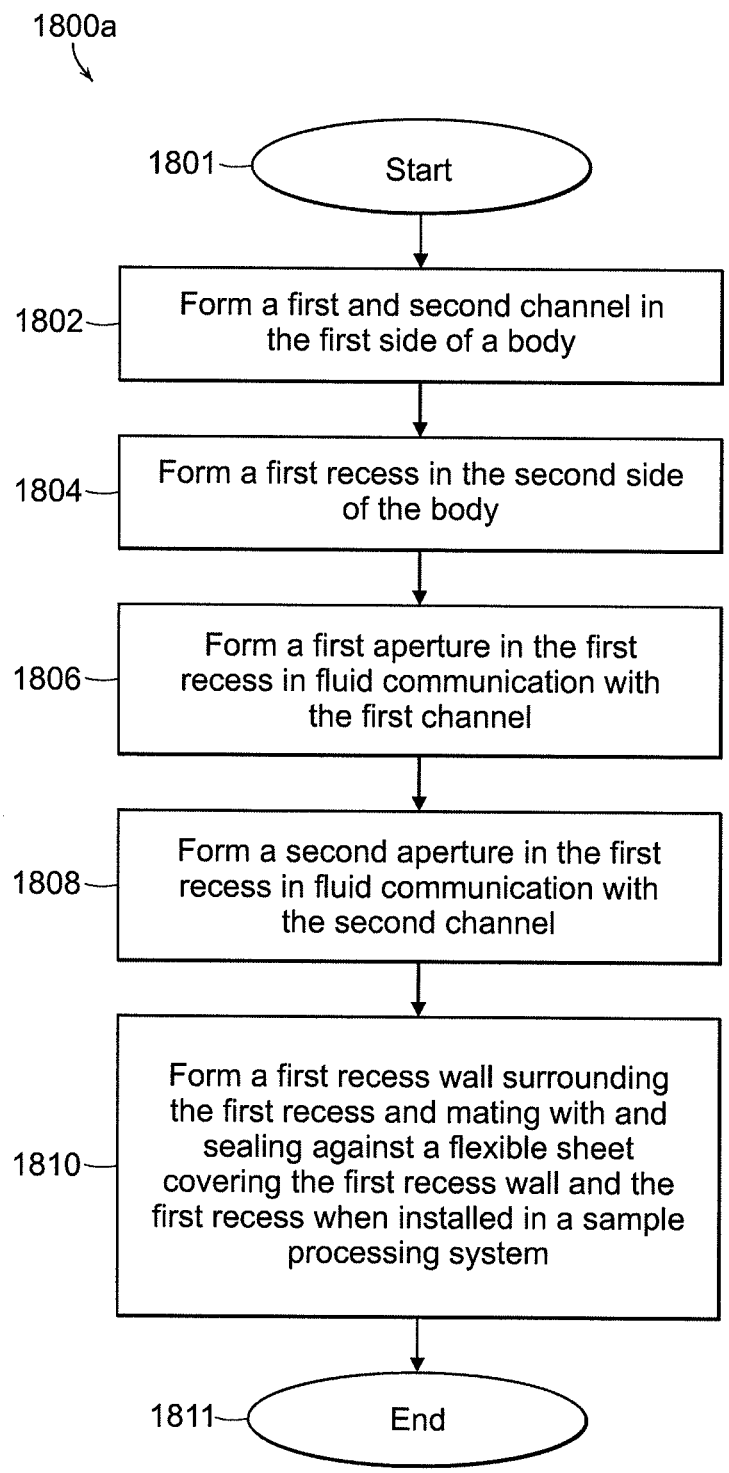
FIG. 18A is a flow diagram of a method for manufacturing a cartridge, according to an illustrative embodiment of the invention.

FIG. 18A is a flow diagram of a process 1800a for manufacturing a portion of a cartridge (e.g., the cartridge 201 of FIG. 6) according to one embodiment. After the process 1800a starts 1801, a first channel (e.g., the processing device output channel 381 of FIG. 6) and a second channel (e.g., the fluid reservoir channel 392 of FIG. 6) are formed in the first side (e.g., the first side 375 of FIG. 6) of a body 1802 (e.g., the body 309 of FIG. 6). Next, a first recess (e.g., the first recess 501 of FIG. 6) is formed in the second side (e.g., the second side 370 of FIG. 6) of the body 1804 (e.g., the body 309 of FIG. 6). Then, a first aperture (e.g., the first aperture 305 of FIG. 6) in fluid communication with the first channel (e.g., the processing device output channel 381 of FIG. 6) is formed in the first recess 1806 (e.g., the first recess 501 of FIG. 6). After the first aperture (e.g., the first aperture 305 of FIG. 6) is formed, a second aperture (e.g., the second aperture 305 of FIG. 6) in fluid communication with the second channel (e.g., the fluid reservoir channel 392 of FIG. 6) is formed in the first recess 1808 (e.g., the first recess 501 of FIG. 6). Before the process 1800a ends, a first recess wall (e.g., the first recess wall 502 of FIG. 6) is formed around the first recess 1810 (e.g., the first recess 501 of FIG. 6).

In one embodiment, forming a first recess (e.g., the first recess 501 of FIG. 6) and a first recess wall (e.g., the first recess wall 502 of FIG. 6) includes forming a protrusion (e.g., the protrusion 602 of FIG. 6) extending from the first side (e.g., the first side 375 of FIG. 6) of the body and forming a recess (e.g., the first recess 501 of FIG. 6) in the protrusion. In this embodiment, the first recess wall (e.g., the first recess wall 502 of FIG. 6) is formed in such a way that it mates with and seals against a flexible sheet (e.g., the flexible sheet 605 of FIG. 6) covering the first recess (e.g., the first recess 501 of FIG. 6) and the first recess wall (e.g., the first recess wall 502 of FIG. 6) when the cartridge (e.g., the cartridge 201 of FIG. 6) is installed in a sample processing system (e.g., the sample processing system 200 of FIG. 2). In another embodiment of the process 1800a, a further step includes forming a valve assembly wall (e.g., the valve assembly wall 520 of FIG. 6) around the combination of the first recess (e.g., the first recess 501 of FIG. 6) and the first recess wall in such a way that the valve assembly wall (e.g., the valve assembly wall 520 of FIG. 6) mates with and seals against the flexible sheet (e.g., the flexible sheet 605 of FIG. 6). In some embodiments, one or more of the above manufacturing steps are performed together.

Figure 18B:
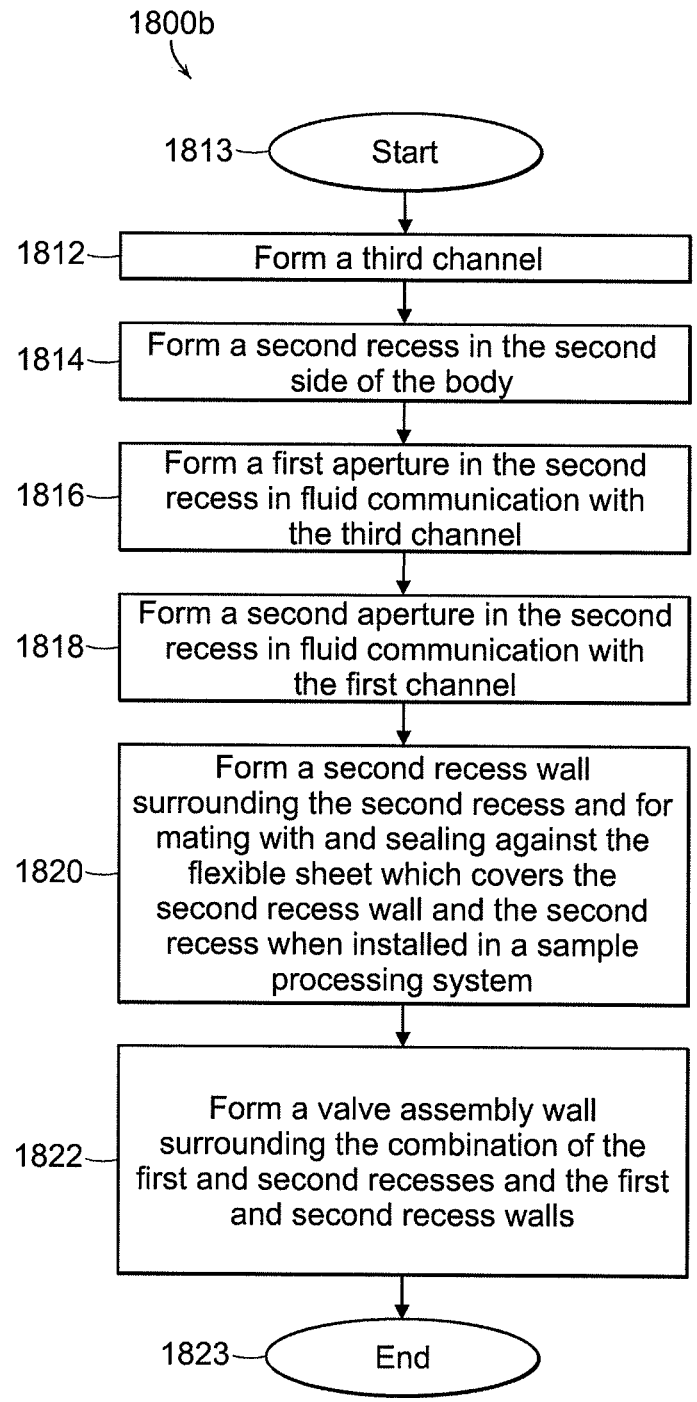
FIG. 18B is a flow diagram of a method for manufacturing a cartridge employed in addition to the method of FIG. 18A, according to another embodiment of the invention.

FIG. 18B is a flow diagram of a method 1800b for manufacturing a cartridge 201 (e.g., the cartridge 201 of FIG. 6) that follows the method of FIG. 18A, according to another embodiment of the invention. The method 1800b starts 1813 after method 1800a ends 1811. A third channel (e.g., the waste output channel 382 of FIG. 6) is formed in the first side (e.g., the first side 375 of FIG. 6) of the body 1812 (e.g., the body 309 of FIG. 6). Next, a second recess (e.g., the second recess 503 of FIG. 6) is formed in the second side of the body 1814 (e.g., the body 309 of FIG. 6). A first aperture (e.g., the second aperture 308 of FIG. 6) in fluid communication with the third channel (e.g., the waste output channel 382 of FIG. 6) is then formed in the second recess 1816 (e.g., the second recess 503 of FIG. 6) and a second aperture (e.g., the first aperture 307 of FIG. 6) in fluid communication with the second channel (e.g., the fluid reservoir channel 392 of FIG. 6) is formed in the second recess 1818 (e.g., the second recess 503 of FIG. 6).

Next, a second recess wall (e.g., the second recess wall 504 of FIG. 6) is formed around the second recess 1820 (e.g., the second recess 503 of FIG. 6). The second recess wall (e.g., the second recess wall 504 of FIG. 6) is formed with a surface that can mate with and seal against a flexible sheet (e.g., the flexible sheet 605 of FIG. 6) that covers the second recess (e.g., the second recess 503 of FIG. 6) and the second recess wall (e.g., the second recess wall 504 of FIG. 6) when the cartridge (e.g., the cartridge 201 of FIG. 6) is installed in a sample processing system (e.g., the sample processing system 200 of FIG. 2). Before the process 1800b ends 1823, a valve assembly wall (e.g., the valve assembly wall 520 of FIG. 6) is formed around the combination of the first and second recesses (e.g., the first and second recesses 501, 503 of FIG. 6) and the first and second recess walls (e.g., the first and second recess walls 502, 504 of FIG. 6). The valve assembly wall (e.g., the valve assembly wall 520 of FIG. 6) is formed in such a way that the valve assembly wall mates with and seals against the flexible sheet (e.g., the flexible sheet 605 of FIG. 6). In some embodiments, a valve assembly wall (e.g., the valve assembly wall 520 of FIG. 6) affixes the flexible sheet (e.g., the flexible sheet 605 of FIG. 6) to the cartridge (e.g., the cartridge 201 of FIG. 6) to cover the recesses (e.g., the first and second recesses 501, 503 of FIG. 6) and the recess walls (e.g., the first and second recess walls 502, 504 of FIG. 6).

Figure 19B:
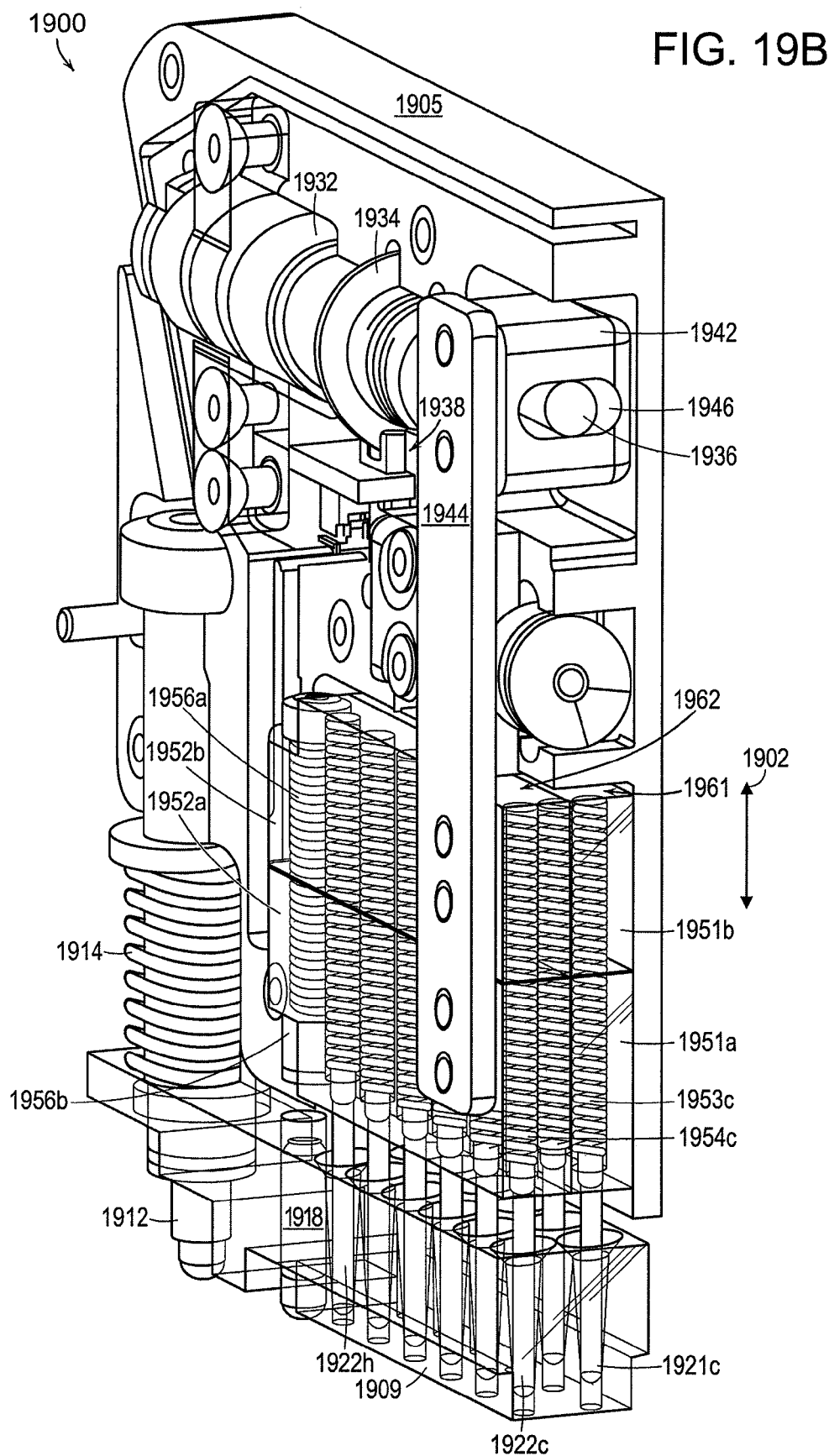
FIG. 19B is a cross-sectional perspective view of the valve actuator assembly of FIG. 19A.

FIG. 19A is a perspective side view of another embodiment of a valve actuator assembly 1900 of a movable head assembly (e.g., the movable head assembly 802 of FIG. 8) with the front cover removed. FIG. 19B is a cross-sectional perspective view of the valve actuator assembly 1900 of FIG. 19A. The valve actuator assembly 1900 includes rough alignment positioning pins 1911, 1912 and fine alignment positioning pins 1917, 1918. The fine alignment positioning pins 1917, 1918 mate and align with corresponding valve assembly positioning apertures of a cartridge (e.g., the input valve assembly positioning apertures 314a, 314b or the output valve assembly positioning apertures 324a, 324b of the cartridge 201 of FIG. 3A). The rough alignment positioning pins 1911, 1912 are attached to the valve actuator assembly block 1905. The rough alignment positioning pins 1911, 1912 mate and align with corresponding apertures in the moving head assembly.

The valve actuator assembly 1900 includes a face seal element 1909 that is coupled to the valve actuator assembly block 1905 via springs 1913, 1914 surrounding the upper portion of the rough alignment positioning pins 1911, 1912. When the movable head assembly engages with the cartridge, the face seal element 1909 mates with a flexible sheet of a cartridge's valve assembly (e.g., the flexible sheet 605 of the output valve assembly 320 of FIG. 6). The movable head assembly applies a force to the face seal element 1909 through the springs 1913, 1914 to seal each of the valves of a cartridge's valve assemblies (e.g., the input valves 311, 312 of the input valve assembly 310 or the output valves 321, 322 of the output valve assembly 320 of FIG. 3A). In another embodiment, the valve actuator assembly 1900 is separately movable with respect to a movable head assembly (e.g., the movable head assembly 802 of FIG. 8) along the vertical axis 1902. The valve actuator assembly 1900 can engage with a cartridge's valve assembly (e.g., the input valve assembly 310 of FIG. 3A) when the valve actuator assembly 1900 is driven by a motor.

The valve actuator assembly 1900 includes a bank of eight first valve pins 1921a-1921h (generally, 1921) and a parallel bank of eight second valve pins 1922a-1922h (generally, 1922). The first valve pins 1921 are positioned through apertures 1923a-1923h (generally, 1923) in the face seal 1909. The second valve pins 1922 are positioned through apertures 1924a-1924h (generally, 1924) in the face seal 1909. The valve actuator assembly 1900 can include a bank of first valve pins or a bank of second valve pins with more or less than eight valve pins. In one embodiment, the valve pins 1921, 1922 are about 0.15875 cm (0.0625 in) in diameter. Each first valve pin 1921 is individually sprung with a corresponding first valve pin spring 1953a-1953h (generally, 1953). The top portion of the first valve pins 1921 and corresponding first valve pin springs 1953 are positioned within apertures in the top first valve pin spring block 1952b and apertures in the bottom first valve pin spring block 1952a. The blocks 1952a, 1952b are coupled together by fastening nut 1956b to bolt 1956a and fastening nut 1966b to bolt 1966a to hold the first valve pins 1921 and first valve pin springs 1953 in place.

Each second valve pin 1922 is individually sprung with a corresponding second valve pin spring 1954a-1954h (generally, 1954). The top portion of the second valve pins 1922 and corresponding second valve pin springs 1954 are positioned within apertures in the top second valve pin spring block 1951b and apertures in the bottom first valve pin spring block 1951a. The blocks 1951a, 1951b are coupled together by fastening nut 1955b to bolt 1955a and fastening nut 1965b to bolt 1965a to hold the second valve pins 1922 and second valve pin springs 1954 in place. In one embodiment, the valve pin springs 1953, 1954 are selected to provide in the range of 2.22 to 4.45 N (0.5 to 1 lb) of sealing force.

The valve actuator assembly 1900 includes a first motor 1931, a first portion of a first cam shaft 1935a, a second portion of the first cam shaft 1935b (i.e., the eccentric portion), and a first slotted bearing block 1941. The valve actuator assembly 1900 also includes a second motor 1932, a first portion of a second cam shaft 1936a, a second portion of the second cam shaft 1936b (i.e., the eccentric portion), and a second slotted bearing block 1942 with a slot 1946. The second motor 1932 drives the second cam shaft 1936 to rotate the second portion of the second cam shaft 1936b in the slot 1946, which causes the second slotted bearing block 1942 to move up or down along the vertical axis 1902. The second slotted bearing block 1942 is attached through a flat, elongated coupling element 1944 to the second valve pin assembly 1962. Thus, the second motor 1932 can move the second valve pin assembly 1962 up or down along the vertical axis 1902 to synchronously lift or lower the spring-loaded second valve pins 1922.

The second portion of the second cam shaft 1936b can be stopped at, or near, the highest or lowest position it can reach along the vertical axis 1902. At or near the highest or lowest position, the longitudinal axis of the second portion of the cam shaft 1948 is vertically aligned directly above or below the longitudinal axis (i.e., center of rotation) of the first portion of the second cam shaft 1936. Thus, the spring forces in the second valve pin springs 1954 of the second valve pin assembly 1962 exert approximately zero torque on the second cam shaft 1936. The second motor 1932 includes a planetary gear head 1972 so that this near-zero torque condition combined with the friction in the planetary gear head ensures that no power is required to maintain the second valve pin assembly 1962 in a lifted or lowered position along the vertical axis 1902.

Similar to the second motor 1932, the first motor 1931 drives the first cam shaft 1935 to rotate the second portion of the first cam shaft 1935b, which causes the first slotted bearing block 1941 to move up or down along the vertical axis 1902. The first slotted bearing block 1941 is attached through a flat, elongated coupling element 1943 to the first valve pin assembly 1961. Thus, the first motor 1931 can move the second valve pin assembly 1961 up or down along the vertical axis 1902 to synchronously lift or lower the spring-loaded first valve pins 1921.

A photo sensor 1937 senses the radial position of the first cam shaft 1935 with respect to the longitudinal axis of the first cam shaft 1935 by sensing the presence of a half moon disk 1933 that is coupled to the first cam shaft 1935. Likewise, a photo sensor 1938 senses the radial position of the second cam shaft 1936 with respect to the longitudinal axis of the second cam shaft 1936 by sensing the presence of a half moon disk 1934 that is coupled to the second cam shaft 1936. In operation, the first motor 1931 drives the second portion of the first cam shaft 1935b in a particular direction until the half moon disk 1933 no longer interrupts the photo sensor 1937, at which point the second portion of the first cam shaft 1935b reaches the highest or lowest position it can reach along the vertical axis 1902. Similarly, the second motor 1932 drives the second portion of the second cam shaft 1936b until the half moon disk 1934 no longer interrupts the photo sensor 1938, at which point the second portion of the second cam shaft 1936b reaches the highest or lowest position it can reach along the vertical axis 1902.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A cartridge for processing a fluid sample, comprising:
   a plurality of fluid inputs defined in the cartridge;
   an input valve assembly defined in the cartridge, the input valve assembly comprising a plurality of input valves, each input valve defined by:
      a recess defined in the cartridge, the recess extending into the cartridge from a surface of the cartridge;
      a wall defined by the cartridge at an intersection of an outer edge of the recess and the surface of the cartridge,
      an input valve inlet defined in the recess, the input valve inlet extending from a surface of the recess into the cartridge, and
      an input valve outlet defined in the recess adjacent the input valve inlet, the input valve outlet extending from the surface of the recess into the cartridge,
   wherein the input valve assembly comprises a membrane disposed over the plurality of input valves, the membrane mating with the wall of each input valve,
   wherein the membrane includes a resting state and an expanded state, (i) the membrane in the resting state, the wall of the input valve, and the recess defining, for each input valve, an input valve fluid chamber through which the fluid sample flows from the input valve inlet to the input valve outlet, and (ii) the membrane in the expanded state protruding into the recess, mating with the surface of the recess, and sealing the input valve inlet from the input valve outlet;
   an output valve assembly defined in the cartridge, the output valve assembly comprising a plurality of first output valves and a plurality of second output valves, each output valve defined by:
      a recess defined in the cartridge, the recess extending into the cartridge from a surface of the cartridge,
      a wall defined by the cartridge at an intersection of an outer edge of the recess and the surface of the cartridge,
      an output valve inlet defined in the recess, the output valve inlet extending from a surface of the recess into the cartridge, and an output valve outlet defined in the recess adjacent the output valve inlet, the output valve outlet extending from the surface of the recess into the cartridge, wherein the output valve assembly comprises a second membrane disposed over the plurality of first output valves and the plurality of second output valves, the second membrane mating with the wall of each output valve, wherein the second membrane includes a resting state and an expanded state, (i) the second membrane in the resting state, the wall of the output valve, and the recess defining, for each output valve, an outlet valve fluid chamber through which the fluid sample flows from the output valve inlet to the output valve outlet, and (ii) the membrane in the expanded state protruding into the recess, mating with the surface of the recess, and sealing the output valve inlet from the output valve outlet;

a plurality of fluid reservoirs defined in the cartridge; and a plurality of processing devices disposed on a surface of the cartridge, each processing device defining a processing device fluid chamber, a processing device inlet, and a processing device outlet, each processing device inlet in fluid communication with the input valve outlet of at least one input valve of the plurality of input valves, each processing device outlet in fluid communication with the output valve inlet of one first output valve of the plurality of first output valves, each first output valve outlet in fluid communication with one fluid reservoir of the plurality of fluid reservoirs and the output valve inlet of one second output valve of the plurality of second output valves;

a plurality of channels defined in the cartridge, each channel configured to transport the fluid sample from a fluid input of the plurality of fluid inputs, through one input valve of the plurality of input valves, through one processing device of the plurality of processing devices, through one first output valve of the plurality of first output valves to one fluid reservoir of the plurality of fluid reservoirs and through one second output valve of the plurality of second output valves.

2. The cartridge of claim 1 wherein the membrane includes a first surface configured to receive a mating surface of a movable head assembly and a second surface configured to mate with the surface of each recess of each input valve and seal the respective input valve inlet from the respective input valve outlet when the mating surface engages the membrane and the membrane is in the expanded state.

3. The cartridge of claim 1 wherein the second membrane includes a first surface configured to receive a mating surface of a movable head assembly and a second surface configured to mate with the surface of each recess of each outlet valve and seal the respective output valve inlet from the respective output valve outlet when the mating surface engages the second membrane and the second membrane is in the expanded state.

4. The cartridge of claim 1, wherein the plurality of processing devices are flexural plate wave devices.

5. The cartridge of claim 1, wherein the plurality of input valves comprise a plurality of reagent input valves and a plurality of fluid input valves.

6. The cartridge of claim 1, further comprising at least one positioning feature.

7. The cartridge of claim 6, wherein the at least one positioning feature comprises at least one aperture defined by a surface of the cartridge.

8. The cartridge of claim 7, further comprising a wall surrounding the at least one aperture and extending from the surface of the cartridge.

9. The cartridge of claim 6, wherein the at least one positioning feature comprises at least one pin disposed on the surface of the cartridge.

10. The cartridge of claim 6, wherein the at least one positioning feature is adapted to align the cartridge with an instrument.

11. The cartridge of claim 10, further comprising at least a second positioning feature adapted to align at least one assembly of a moveable head assembly with a portion of the cartridge.

12. The cartridge of claim 11, wherein the portion of the cartridge includes the input valve assembly.

13. The cartridge of claim 1, wherein each fluid reservoir comprises a chamber having an aperture and a wall, the wall surrounding the aperture and extending from an exterior surface of the chamber, the wall adapted to align, mate, and seal with a pump interface member.

14. The cartridge of claim 13, wherein the wall is adapted to receive a gas permeable, liquid impermeable element.

15. The cartridge of claim 14, wherein the element is a membrane or a filter.

16. The cartridge of claim 2 wherein the first surface of the membrane is configured to receive a plurality of pins protruding from the mating surface of the movable head assembly, the plurality of pins expanding the membrane so that the second surface seals the respective input valve inlet from the respective input valve outlet.

17. The cartridge of claim 3 wherein the first surface of the second membrane is configured to receive a plurality of pins protruding from the mating surface of the movable head assembly, the plurality of pins expanding the second membrane so that the second surface seals the respective output valve inlet from the respective output valve outlet.

18. A cartridge for processing a fluid sample, comprising:
a valve assembly defined in the cartridge, the valve assembly comprising a plurality of valves, each valve defined by:
a recess defined in the cartridge, the recess extending into the cartridge from a surface of the cartridge;
a wall defined by the cartridge at an intersection of an outer edge of the recess and the surface of the cartridge;
a valve inlet defined in the recess, the valve inlet extending from a surface of the recess into the cartridge; and
a valve outlet defined in the recess adjacent the valve inlet, the valve outlet extending from the surface of the recess into the cartridge;

wherein the valve assembly comprises a membrane disposed over the plurality of valves, the membrane mating with the wall of each valve, wherein the membrane includes a resting state and an expanded state, (i) the membrane in the resting state, the wall of the valve, and the recess defining, for each valve, a valve fluid chamber through which the fluid sample flows from the valve inlet to the valve outlet, and (ii) the membrane in the expanded state protruding into the recess, mating with the surface of the recess, and sealing the valve inlet from the valve outlet;

a plurality of processing devices disposed on a surface of the cartridge, each processing device in fluid communication with at least one valve of the valve assembly via a fluid conduit defined in the cartridge.

19. A system for processing a sample, the system comprising:

a cartridge comprising:
- a plurality of fluid interfaces;
- a plurality of channels;
- a valve assembly defined in the cartridge, the valve assembly comprising a plurality of valves, each valve defined by:
  - a recess defined in the cartridge, the recess extending into the cartridge from a surface of the cartridge;
  - a wall defined by the cartridge at an intersection of an outer edge of the recess and the surface of the cartridge;
  - a valve inlet defined in the recess, the valve inlet extending from a surface of the recess into the cartridge; and
  - a valve outlet defined in the recess adjacent the valve inlet, the valve outlet extending from the surface of the recess into the cartridge;
  - wherein the valve assembly comprises a membrane disposed over the plurality of valves, the membrane mating with the wall of each valve,
  - wherein the membrane includes a resting state and an expanded state, (i) the membrane in the resting state, the wall of the valve, and the recess defining, for each valve, a valve fluid chamber through which the fluid sample flows from the valve inlet to the valve outlet, and (ii) the membrane in the expanded state protruding into the recess, mating with the surface of the recess, and sealing the valve inlet from the valve outlet;
- a plurality of processing devices disposed on a surface of the cartridge, each processing device in fluid communication with at least one valve of the valve assembly via a fluid conduit defined in the cartridge;
- a plurality of fluid reservoirs; at least one channel providing fluid communication between at least one of the fluid interfaces and at least one of the fluid reservoirs through at least one of the valves;
- a movable head assembly comprising a valve interface assembly adapted to apply a force to the valve assembly to form a sealed fluid chamber in each of the plurality of valves, the valve interface assembly comprising a plurality of movable members each adapted to open and close fluid communication between the valve inlet and the valve outlet of at least one of the plurality of valves; and
- a pump comprising a plurality of pump interface members each adapted (1) to mate and align with a corresponding one of the plurality of fluid reservoirs and (2) to move a sample between at least one fluid interface and at least one fluid reservoir through at least one channel and at least one valve across a processing device.

20. The system of claim 19, wherein at least one movable member is adapted to provide zero-hold power actuation to each corresponding valve.

* * * * *